(12) United States Patent
Muller

(10) Patent No.: US 10,219,697 B2
(45) Date of Patent: Mar. 5, 2019

(54) SYSTEMS AND METHODS FOR ELECTROCORTICOGRAPHY SIGNAL ACQUISITION

(71) Applicant: THE REGENTS OF THE UNIVERSITY OF CALIFORNIA, Oakland, CA (US)

(72) Inventor: Rikky Muller, Kirkland, WA (US)

(73) Assignees: The Regents of the University of California, Oakland, CA (US); Cortera Neurotechnologies, Inc., Berkeley, CA (US)

( * ) Notice: Subject to any disclaimer, the term of this patent is extended or adjusted under 35 U.S.C. 154(b) by 0 days.

(21) Appl. No.: 15/044,965

(22) Filed: Feb. 16, 2016

(65) Prior Publication Data

US 2016/0242645 A1  Aug. 25, 2016

Related U.S. Application Data

(63) Continuation of application No. PCT/US2014/051959, filed on Aug. 20, 2014.
(Continued)

(51) Int. Cl.
*A61B 5/00* (2006.01)
*A61N 1/37* (2006.01)
(Continued)

(52) U.S. Cl.
CPC ........ *A61B 5/0006* (2013.01); *A61B 5/04004* (2013.01); *A61B 5/04017* (2013.01);
(Continued)

(58) Field of Classification Search
CPC ......... A61B 5/0476; A61B 5/048; A61B 5/04; A61B 5/04004; A61B 5/0402;
(Continued)

(56) References Cited

U.S. PATENT DOCUMENTS 4,291,299 A * 9/1981 Hinz ...................... H03M 1/127
341/123
4,293,820 A * 10/1981 Dinh .................. H03H 11/1217
330/109
(Continued)

FOREIGN PATENT DOCUMENTS

EP        0 568 197 A2    11/1993
KR   10-2009-0029854 A    3/2009
(Continued)

OTHER PUBLICATIONS

Martens et al., "High-performance analogue measurement using internal enhanced PWM and ADC of a DSP-chip," Intelligent Signal Processing, 2007, WISP 2007. IEEE International Symposium on, Alcala de Henares, 2007, pp. 1-5.*
(Continued)

*Primary Examiner* — Michelle M Koeth
(74) *Attorney, Agent, or Firm* — Charles D. Gavrilovich, Jr.; Gavrilovich, Dodd & Lindsey LLP

(57) ABSTRACT

Systems and methods for biosignal acquisition, and in particular, electrocorticography signal acquisition, are disclosed for small area, low noise recording and digitization of brain signals from electrode arrays.

14 Claims, 20 Drawing Sheets

Related U.S. Application Data

(60) Provisional application No. 61/867,899, filed on Aug. 20, 2013.

(51) Int. Cl.
*A61B 5/04* (2006.01)
*A61B 5/0476* (2006.01)
*H04L 27/06* (2006.01)
*A61B 5/048* (2006.01)
*A61B 5/0478* (2006.01)

(52) U.S. Cl.
CPC .......... *A61B 5/0476* (2013.01); *A61B 5/7203* (2013.01); *A61B 5/7228* (2013.01); *A61N 1/3704* (2013.01); *H04L 27/06* (2013.01); *A61B 5/048* (2013.01); *A61B 5/0478* (2013.01)

(58) Field of Classification Search
CPC . A61B 5/7203; A61B 5/7228; A61B 5/04017; A61B 5/0478; A61B 5/0006; A61N 1/3704; G06F 3/015; H03H 11/1295; H04L 27/06
See application file for complete search history.

(56) References Cited

U.S. PATENT DOCUMENTS

| | | | | |
|---|---|---|---|---|
| 7,623,053 B2 * | 11/2009 | Terry | ................ | A61N 1/3704 341/143 |
| 7,676,239 B1 * | 3/2010 | Doyle | ................ | H04W 52/52 455/114.3 |
| 9,248,288 B2 * | 2/2016 | Panken | ................ | A61N 1/36139 |
| 2008/0284490 A1 | 11/2008 | Tenbroek | | |
| 2009/0072873 A1 * | 3/2009 | Denier | ................ | H03K 5/003 327/175 |
| 2009/0079607 A1 * | 3/2009 | Denison | ................ | A61B 5/04012 341/143 |
| 2011/0193731 A1 | 8/2011 | Jorg et al. | | |
| 2012/0194369 A1 * | 8/2012 | Galton | ................ | H03M 3/388 341/120 |

FOREIGN PATENT DOCUMENTS

| | | | |
|---|---|---|---|
| WO | 2006/050325 A2 | 5/2006 | |
| WO | 2011/047381 A1 | 4/2011 | |

OTHER PUBLICATIONS

Muller et al., "A 0.013 mm2, 5 μW, DC-Coupled Neural Signal Acquisition IC With 0.5 V Supply," IEEE Journal of Solid-State Circuits, vol. 47, No. 1, Jan. 2012.*
Muller et al., "A 0.013 mm2, 5 pW, DC-Coupled Neural Signal Acquisition 1C With 0.5 V Supply," IEEE Journal of Solid-State Circuits, vol. 47, No. 1, Jan. 2012.*
Korean Intellectual Property Office (KIPO), International Search Report and Written Opinion, dated Nov. 21, 2014, PCT/US2014/051959, pp. 1-12, with claims searched, pp. 13-16. The US application filed herein is a continuation of PCT/US2014/051959. The relevance of non-English language reference KR 10-2009-0029854 is indicated in the foregoing International Search Report and Written Opinion and, therefore, a separate concise statement of relevance is not required.

* cited by examiner

SYSTEMS AND METHODS FOR ELECTROCORTICOGRAPHY SIGNAL ACQUISITION

CROSS-REFERENCE TO RELATED APPLICATIONS

This application is a 35 U.S.C. § 111(a) continuation of PCT international application number PCT/US2014/051959 filed on Aug. 20, 2014, incorporated herein by reference in its entirety, which claims priority to, and the benefit of, U.S. provisional patent application Ser. No. 61/867,899 filed on Aug. 20, 2013, incorporated herein by reference in its entirety. Priority is claimed to each of the foregoing applications.

The above-referenced PCT international application was published as PCT International Publication No. WO 2015/026988 on Feb. 26, 2015, which publication is incorporated herein by reference in its entirety.

STATEMENT REGARDING FEDERALLY SPONSORED RESEARCH OR DEVELOPMENT

This invention was made with Government support under HR0011-07-3-0002 awarded by the Defense Advanced Research Projects Agency (DARPA). The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

This invention pertains generally to signal acquisition, and more particularly to neural signal acquisition.

2. Background Discussion

Chronic brain-computer interfaces are an emerging technology that aim at restoring motor or communication function in individuals with spinal chord injuries and/or neurodegenerative diseases. Electrocorticography (ECoG) is a brain-recording modality that utilizes non-penetrating (e.g. sub-dural or epidural electrodes), and shows particular promise for future brain computer interfaces as it can provide similar spatial resolution to more invasive techniques, but reduces scar-tissue formation and hence enables longer-term recordings.

An integral part of every brain-machine interface system is an amplifier/digitizer system that converts the brain activity picked up by the electrodes to digital signals for further processing and/or transmission. The main challenge in the design of such a subsystem is to provide low input-referred noise while avoiding loading excessively the high impedance electrodes and while preventing the large offset associated with the electrode-tissue interface from saturating the electronics. Current solutions design the amplifying and digitizing functions separately and use large passive components, leading to an un-economically large footprint for the electronics.

State-of-the-art ECoG and EEG amplifiers occupy a large portion of die area due not only to the input AC coupling capacitors employed but also to the feedback capacitors that are used to cancel the upmodulated offset at the summing node. While good power efficiencies have been achieved, the resulting die area per amplifier can make arrayed implementations beyond approximately eight amplifiers impractical. Accordingly, there is a need to be able to substantially shrink the die area of ECoG neural amplifiers and front-end circuits while maintaining or improving power efficiency.

BRIEF SUMMARY

Accordingly, aspects of the present disclosure are novel circuit architectures and methods for electrocorticography (ECoG) or electroencephalography (EEG) or Action Potential signal acquisition that enable small area, low noise recording and digitization of brain signals from ECoG or EEG electrode arrays. The architectures and methods of the present disclosure enable conversion of microelectrode signals of interest into digital words using extremely low power and low area using a mixed-signal approach and implementation within a low-voltage environment.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

DETAILED DESCRIPTION

The present disclosure is directed to circuit architectures and methods for neurological and biological signal acquisition such as electroencephalography (EEG) electrocorticography (ECoG). By way of example and not of limitation, a functional block diagram for an improved architecture for an ECoG front-end (e.g. amplifier/digitizer system) 10 according to one embodiment of the invention is shown in FIG. 1.

Figure 1:
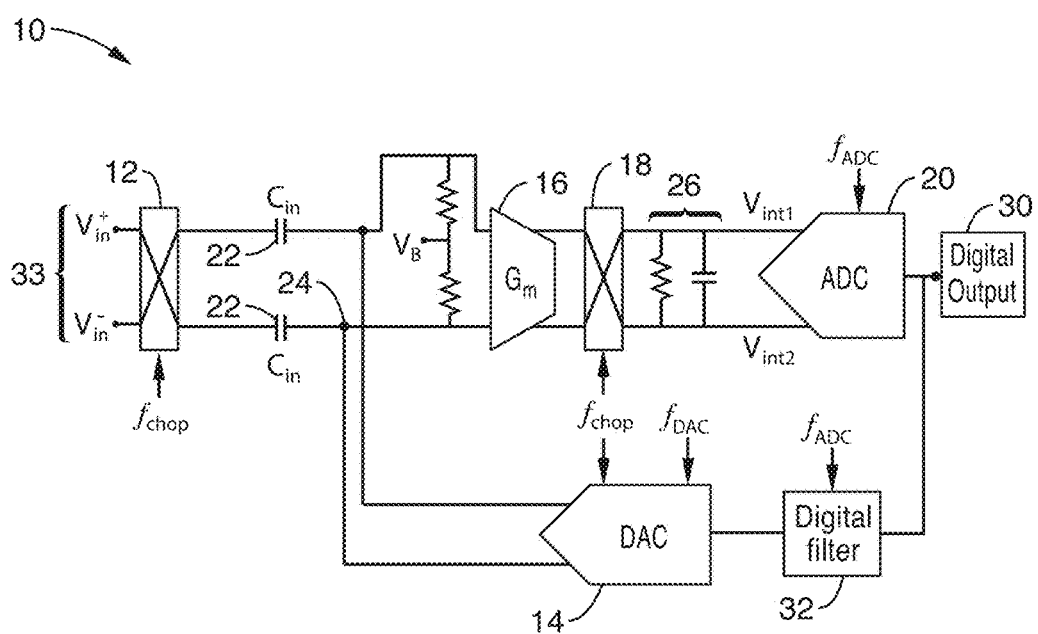
FIG. 1 is a schematic diagram of an amplifier/digitizer front-end system for ECoG or EEG signal acquisition.

The ECoG front-end 10 illustrated in FIG. 1 generally comprises a chopper-stabilized, open-loop amplifier. The amplifier comprises input up-modulation chopper switches 12, a Gm stage 16, down-modulation chopper switches 18 and an R-C filter load 26. The output of the amplification stage 33 is connected to an ADC 20. In a preferred embodiment, the ADC 20 comprises a VCO-based ADC. Shown in greater detail in FIG. 2, VCO-ADC 20 uses a voltage to current converter to drive a ring oscillator 52a/52b whose output is fed into a counter 56a/56b for quantization. The quantization sample is taken at every clock cycle (clock 58a/58b) and subtracted from the previous quantization level to produce the digital output 30. This digital output 30, which comprises the output of the complete system, is then fed back to the input through a digital filter 32 (e.g. an IIR low-pass filter such as an integrator). In preferred embodiment, the digital filter output is then delta-sigma modulated at encoder 34 (see FIG. 10) and fed back to the input through an oversampled capacitor DAC 14. The DAC 14 output is also upmodulated through chopper switches 36 so that the cancellation occurs in the up-modulated signal domain (see FIG. 10). The summation of the DAC 14 and the input signal ($V_{in}^+$, $V_{in}^-$) occurs at junction 24 after the input capacitors 22 and the feedback DAC capacitors 38 (see also FIG. 10), at the input of the Gm amplification stage 16.

To achieve low 1/f noise, the DAC 14 is implemented by passive components as opposed to transistors. In this context, "low 1/f noise" means that the ratio of noise contributed by 1/f noise sources to the total input-referred noise is "low" defined as <10% of the total in this case but can be as much as 50% in practice and still considered "low".

The passive components used in this embodiment are preferably capacitors. In one exemplary configuration, 40 fF unit capacitors may be used, but the component size can be as low as 10 fF or even smaller depending on layout parasitics. The total DAC capacitance in such configuration is 1.24 pF on each side.

The upmodulated offset is mitigated using a mixed-signal feedback loop that uses capacitors on the summing junction 24 to cancel the offset. Capacitor values are substantially reduced since the open-loop architecture allows the capacitors to act as summing rather than pole-setting elements. The capacitor sizes are therefore only limited by layout considerations and parasitic capacitance on the summing node. On-chip 1 nF capacitors may be used to perform the integration, e.g., for use in the digital feedback. This results in a reduction of the capacitance for the feedback loop by nearly three orders of magnitude. The DAC unit capacitors 38 should ideally be sized larger than the summation node parasitic capacitance; otherwise the unit step size is degraded. In practice, this only results in a gain error and is therefore not a hard limit. It is, however, preferred in order to maintain the full scale of the DAC.

The forward path of the architecture comprises a broadband instrumentation amplifier and a VCO-based ADC. The mixed-signal feedback loop provides a $1^{st}$ order high-pass roll-off at around 1 Hz, while the low-pass filter roll-off is provided by the ADC 20 itself. Sampled at 1 kS/s, there is a cut-off at 500 Hz. There is an additional high-pass roll-off, which can be seen in the closed-loop transfer function due to the sinc transfer function of the ADC 20.

Technically, any ADC architecture can be used, but the advantages of using a VCO-based ADC 20 are outlined below and later in this disclosure. Those advantages include:

(1) it uses low up-front gain due to a high inherent ADC gain;

(2) the mostly digital implementation gives low area and low energy per bit; and (3) the inherent sinc transfer function of ADC 20 suppresses chopper ripple, delta-sigma noise and other clock-based interferers.

Figure 2:
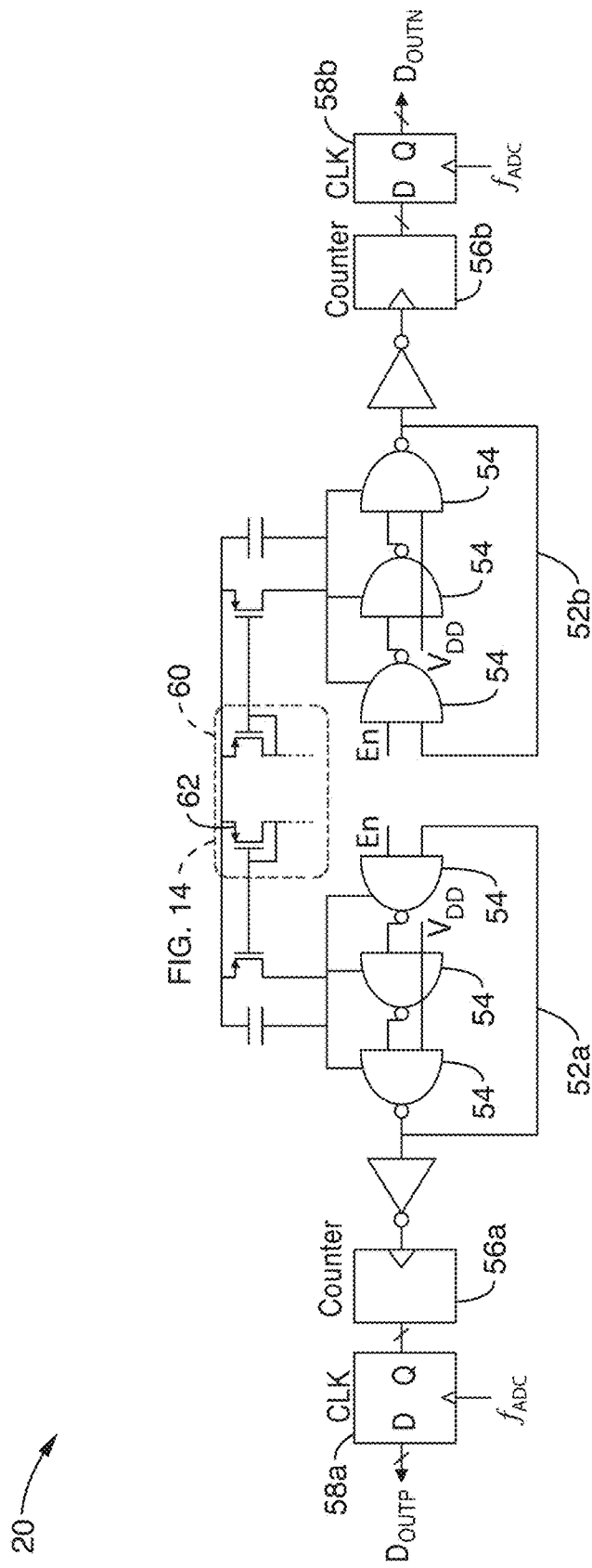
FIG. 2 is a schematic circuit diagram of an exemplary ring-oscillator based ADC for use with the system of FIG. 1.
Figure 3:
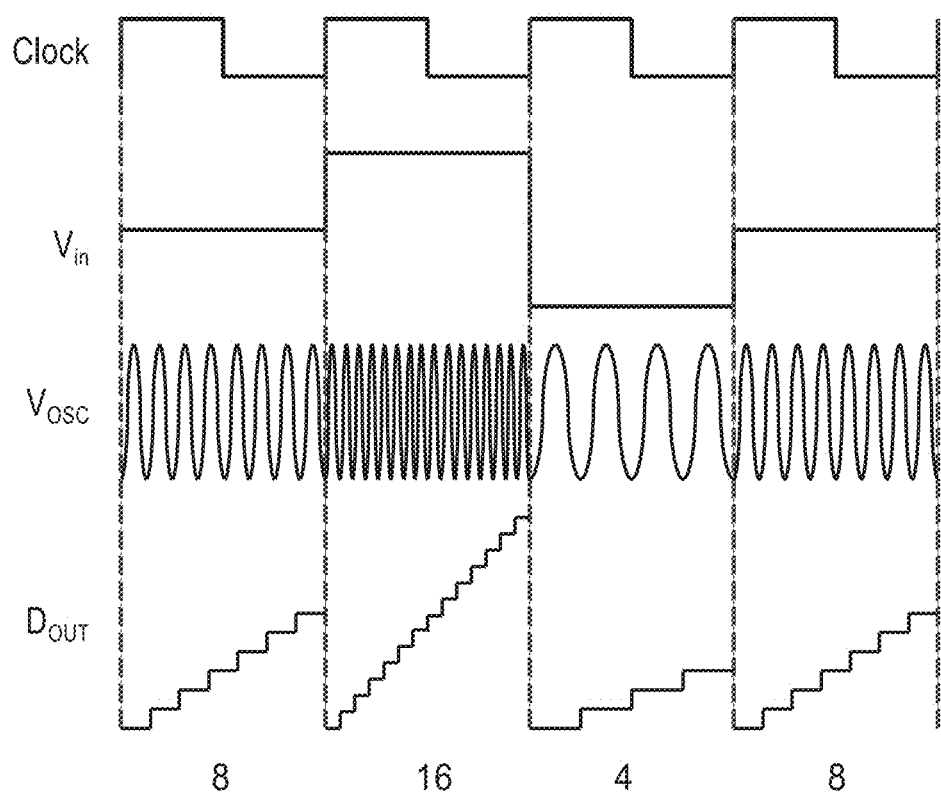
FIG. 3 illustrates exemplary ring-oscillator based ADC operation as provided in the ADC of FIG. 2.

FIG. 2 illustrates a ring-oscillator based ADC 20 and FIG. 3 illustrates operation of the ring-oscillator based ADC 20. The ADC 20, as shown in FIG. 2, employs a pseudo-differential, current-driven, VCO-based architecture. The positive and negative driver output currents are used as the bias for two single-ended, three-stage CMOS ring oscillators 52a/52b realized with NAND gates 54, which feed the clock 58a/58b inputs of 9-bit digital counters 56a/56b. The ADC driver 60 and variable gain are shown in greater detail in FIG. 14A and FIG. 14B.

The basic operation of ring-oscillator based ADC 20 is illustrated in FIG. 3, where an input voltage $V_{IN}$ is used to modulate the oscillation frequency of a ring-oscillator. The number of cycles in a clock period are then quantized by a digital counter. In this implementation the counters are not reset, but allowed to wrap, causing first-order noise shaping of the quantization noise.

Power and area are minimized by the use of simple CMOS rings while supply and common-mode disturbances are suppressed by the differential operation of the circuit. Driving the ADC in the current-domain through a PMOS current mirror further improves power supply rejection ratio (PSRR) and soft-rail operation maintains good linearity through the full dynamic range. While extra resolution can be obtained by sampling all of the oscillator phases, the intrinsic speed of the CMOS technology can be used.

The ring oscillator based ADC 20 exhibits boxcar sampling, which prevents aliasing of the instrumentation amplifier noise, while also removing chopper ripple and suppressing delta-sigma noise. To take advantage of this effect, both $f_{chop}$ and $f_{\Delta\Sigma}$ clock frequencies are placed at harmonic multiples of $f_{ADC}$ where the nulls of the sinc transfer function eliminate chopper ripple and suppress delta-sigma noise, thereby eliminating the need for a ripple reduction loop and extensive anti-alias filtering.

Figure 14A:
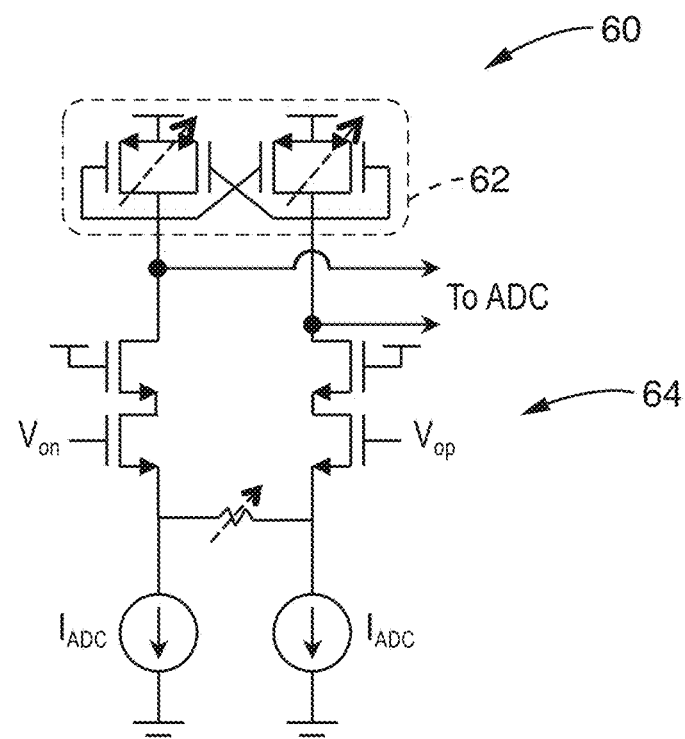
FIG. 14A is a schematic diagram of an ADC driver amplifier.
Figure 14B:
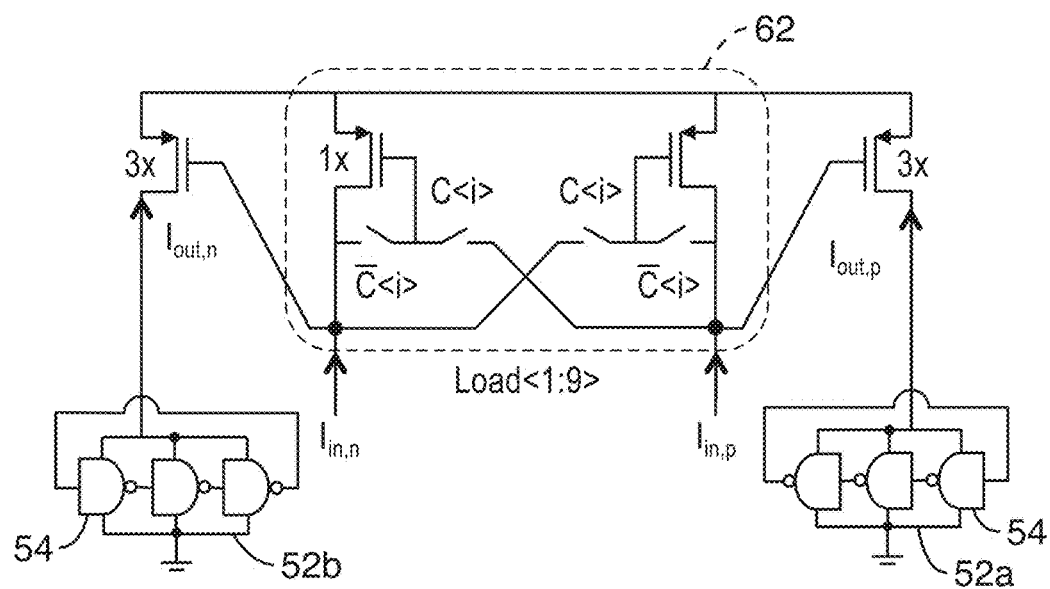
FIG. 14B is an expanded schematic diagram of the ADC driver amplifier of FIG. 14A.

In order to keep the quantization noise well below the thermal noise floor, an ADC resolution of at least 12 bits is preferred. A 13-bit range is provided by each of the ring oscillators 52a/52b at 1 kS/s. Each oscillator is designed such that the minimum and maximum oscillation frequencies $f_{min}$ and $f_{max}$ satisfy $|f_{max}-f_{min}|>2^{13} f_s$ with $f_s=1$ kHz. The counters are preferably not reset with each clock period and are allowed to wrap. Digital correction is implemented to unwrap the codes prior to subtraction. The driver 60 includes a differential-pair V-to-I converter cascaded with a current-mode programmable gain block 62, as shown in FIG. 14A. Variable degeneration resistors are used to further trade-off gain for linearity. Since chopping does not reduce the 1/f noise of this stage, all devices are sized with large area for the purpose of reducing the noise corner.

The counter output represents the average oscillator frequency over a period, corresponding to integration in the time domain and a sinc transfer function in the frequency domain. Thus, the converter provides the desired boxcar sampling response, preventing aliasing of the wideband noise from the instrumentation amplifier. Sinc filters have been used as anti-aliasing filters in this context, but with large-area analog implementation. The system of the present disclosure thus effectively merges an anti-aliasing filter into an ADC in a compact form factor. The box-car sampling characteristic introduces a second key benefit in the system 10, as it suppresses the shaped quantization noise from the Delta-Sigma (DS) DAC 14 employed for offset cancellation, as well as voltage ripple that may result from chopper stabilization.

Essentially, the integrating characteristic of the ADC 20 averages the DAC 14 output bit-stream while performing the conversion, acting as a first stage of decimation. As a result, the high-frequency quantization noise from the DS DAC is greatly attenuated at the output port and does not degrade the overall system SNR.

The feedback path comprises a digital accumulator and a DAC, which realize a servo-loop that suppresses a 100 mV offset below the thermal noise floor (~1 uVrms).

Feedback forces the output of the digital low-pass filter 32 to track the low-frequency components reducing the dynamic range requirement of the instrumentation amplifier and ADC cascade. In this context, low frequency means frequencies below the designed high-pass filter pole. In the present embodiment, this is approximately <1 Hz. If the offset is digitized, then the dynamic range required is reduced by approximately 100× higher (~7 bits).

The mixed-signal feedback loop generally takes the place of an analog integrator, allowing the large time constant generally needed to cancel DC to be once again realized in a compact footprint using digital gates. Again, this is meant to suppress the DC (~100 mV) below the thermal noise floor (~1 uV). The time constant is approximately 1 second in the presented implementation, but can be 10 or even 100× higher.

The system 10 of FIG. 1 exhibits low area, programmability and "per-pixel" digitization, which eliminates the complicated routing of analog signals at the top level. The efficient realization of this architecture presents a few new challenges that are discussed in detail in the following sections.

Novel mixed-signal and digital circuit techniques are implemented in the system of the present disclosure to efficiently implement the large time constants required for filtering in a fine-line process. The mixed-signal architectural configuration of the system of the present disclosure allows for an order of magnitude in area reduction over existing systems, while maintaining or improving upon the low-noise, power-efficient performance. Implementing the architectural configuration of the system of the present disclosure with a low supply voltage of 0.5V also beneficially achieves very low power performance.

Figure 4A:
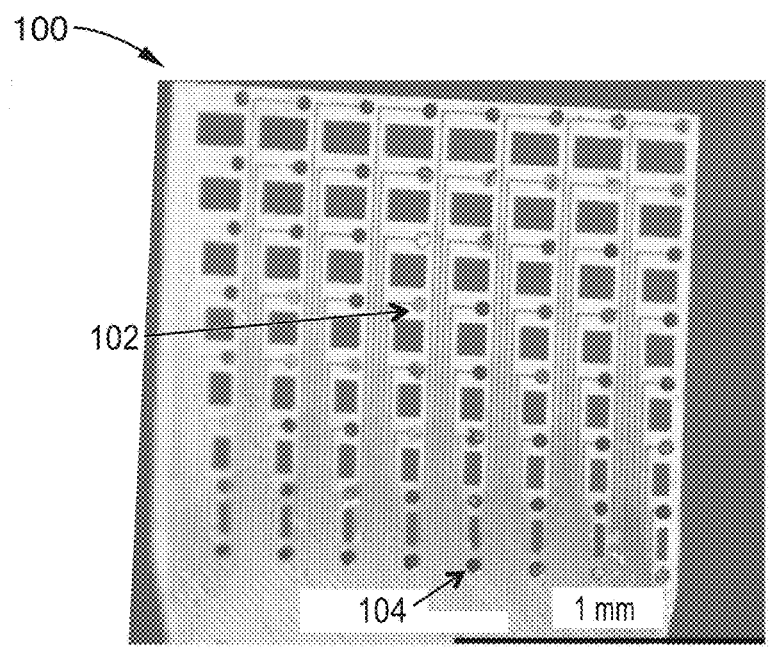
FIG. 4A and FIG. 4B show an image of an array of ECoG electrodes with every other electrode electroplated with platinum black, along with a graph of the impedance of the electrodes at 1 kHz, respectively.
Figure 4B:
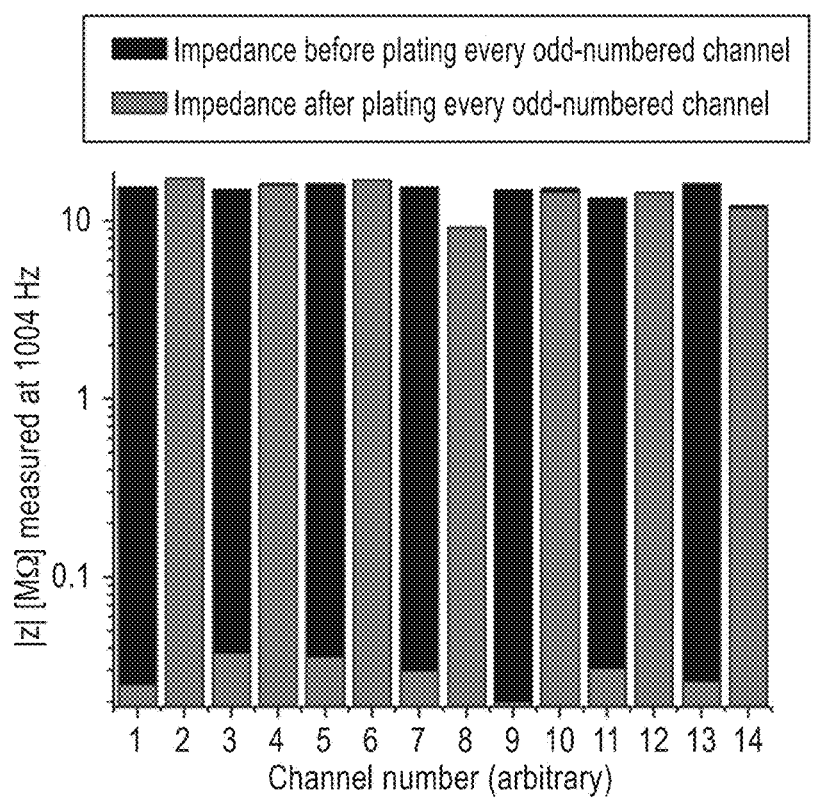

Referring now to FIG. 4A and FIG. 4B, the front-end 10 is ideally to be used with any passive biological electrodes, such as those designed for cortical, ECoG and EEG recording micro-ECoG electrodes. For the design of micron-scale ECoG, the small surface area of the microfabricated ECoG electrodes leads to a high input impedance that also calls for a high front-end input impedance, making such interface quite demanding.

High-density microfabricated ECoG electrodes have been demonstrated using standard thin-film processing techniques. The electrodes reported in yield a resistance of approximately 30 MΩ at 1 kHz and a resistance of 1-10 GΩ at DC. The goal of designing the input impedance of the front-end is to pass the in-band signal without loading the electrodes, whereas loading the electrodes at DC can have a positive effect. In-band input impedances between 10 to 100 MΩ would call for an input impedance of >1 GΩ for the recording electronics, making a chopper stabilized implementation impractical. Additionally, long traces of high-impedance electrodes degrade system performance, since they contribute thermal noise and are susceptible to crosstalk and coupling from interferers.

In order to improve the electrical coupling to the brain, platinum black is electroplated on the surface of the electrodes. Platinum black is a highly porous, conductive material, which effectively increases the surface area of the electrode. For equal diameter, the impedance of platinum black electrodes is more than two orders of magnitude smaller than their platinum counterpart. FIG. 4A shows a microfabricated ECoG grid 100 with platinum black electroplated to every other electrode (i.e., non-plated electrodes 102 are disposed between platinum plated electrode 104 in the ECoG grid 100).

Referring to the plot of FIG. 4B, the corresponding impedance of each electrode is plotted at 1 kHz showing a 1000× reduction in impedance. The impedance of the platinum black electrodes at 1 Hz is on average approximately 300 kΩ. For these electrodes, in order to pass the signal band 1 Hz to 500 Hz, the input impedance of the amplifier would ideally be two orders of magnitude higher which is equal 30 MΩ, although lower is sufficient. While 30 MΩ is more than an order of magnitude lower than the requirement for the action-potential front-end, it nonetheless remains a challenge to meet with a chopper-stabilized front-end since switching capacitance results in very low impedances.

Open-circuit potentials in the hundreds of mV have been observed for platinum black electrodes in solution. The DC resistance of the electrodes are measured and calculated to be on the order of GΩs, therefore an input impedance on the order of 10 MΩ will diminish the offset to <10 mV. 100 mV of offset cancellation range was allocated to the system. Given this full-scale voltage of the DAC, it is first important to determine how many bits of resolution are necessary.

To save area and capacitance at the input an oversampled, Delta-Sigma modulated DAC is implemented. In addition to determining the total resolution necessary, the partition between physical bits and oversampled bits must also be determined. Since the DAC feeds back to the input, its quantization noise must be low enough that it does not impact the noise floor of the amplifier. Take for example the quantization noise of a single-bit DAC.

Figure 5:
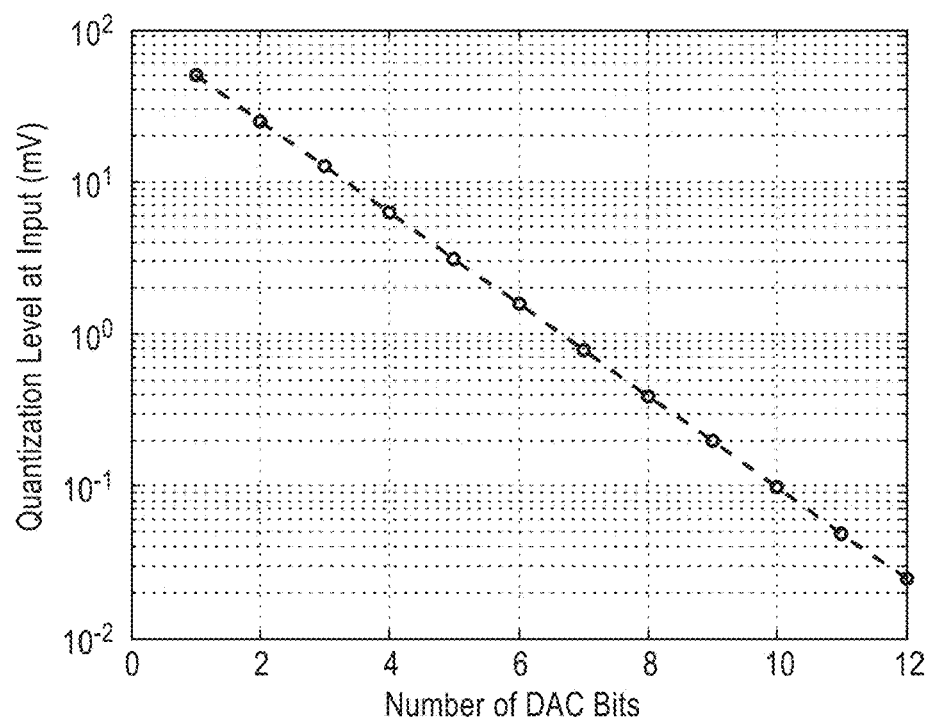
FIG. 5 is a plot of the input quantization voltage level vs. number of DAC bits.

FIG. 5 illustrates a plot of the input quantization voltage level vs. number of DAC bits. FIG. 5 shows that the amplifier would have to be able to handle swings of ±50 mV at its input. Such swings would clearly saturate the forward-path electronics.

Figure 6:
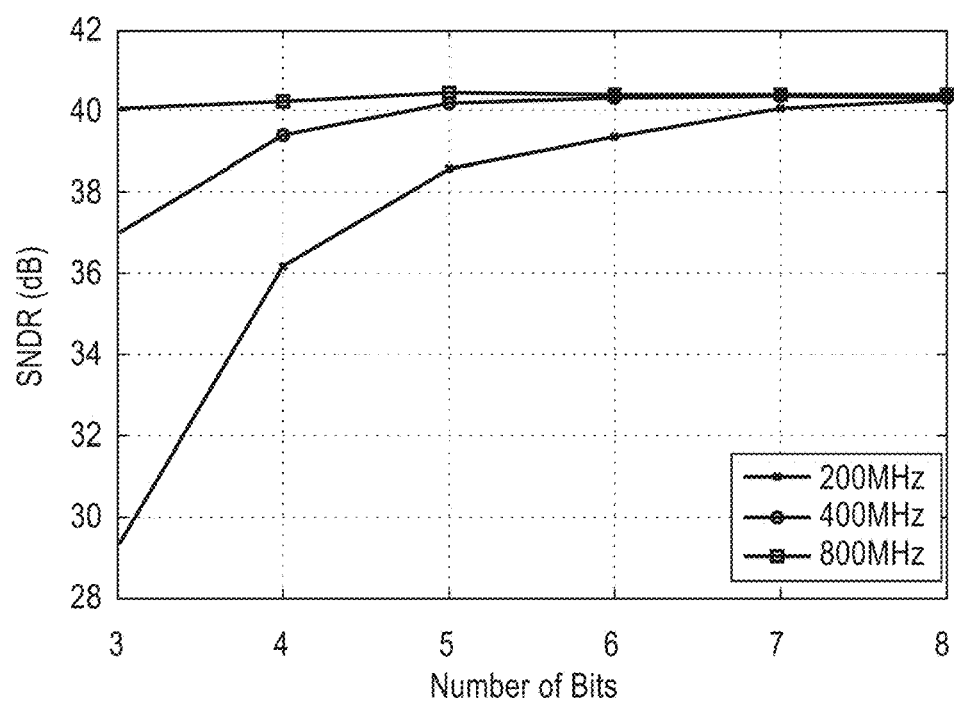
FIG. 6 is a plot of the SNDR vs. number of DAC bits for various DAC frequencies in open-loop.

Using a behavioral simulation in Simulink, the number of physical DAC bits was swept for various DAC clock frequencies. FIG. 6 shows an open-loop simulation of the ECoG band signal-to-noise and distortion ratio (SNDR) vs. the number of bits in the DAC across several frequencies. A 1 µV noise floor and 100 µV mid-band signal was used for the simulation. To suppress the DAC quantization noise below the amplifier noise floor, a delta-sigma clock frequency of at least 800 kHz is used. 1 MHz was chosen for system simplicity and ease of filtering, which will be discussed in further detail below.

Since the input of the amplifier 16 is broadband, a square wave can approximate the quantization noise seen at the input. 1 MHz square waves of varying amplitude were injected at the input of the amplifier in transistor-level simulation to determine the maximum DAC quantization level before there is a noticeable increase in the amplifier noise floor. This quantity was determined to correspond to 5 bits. A full resolution of nearly 20 bits in the feedback DAC 14 is realized with a 5-bit physical DAC with an oversampling ratio (OSR) of 1000. This corresponds to a quantization level of 0.1 µV, small enough to suppress the quantization noise below the thermal noise floor of the front-end 10.

Figure 7:
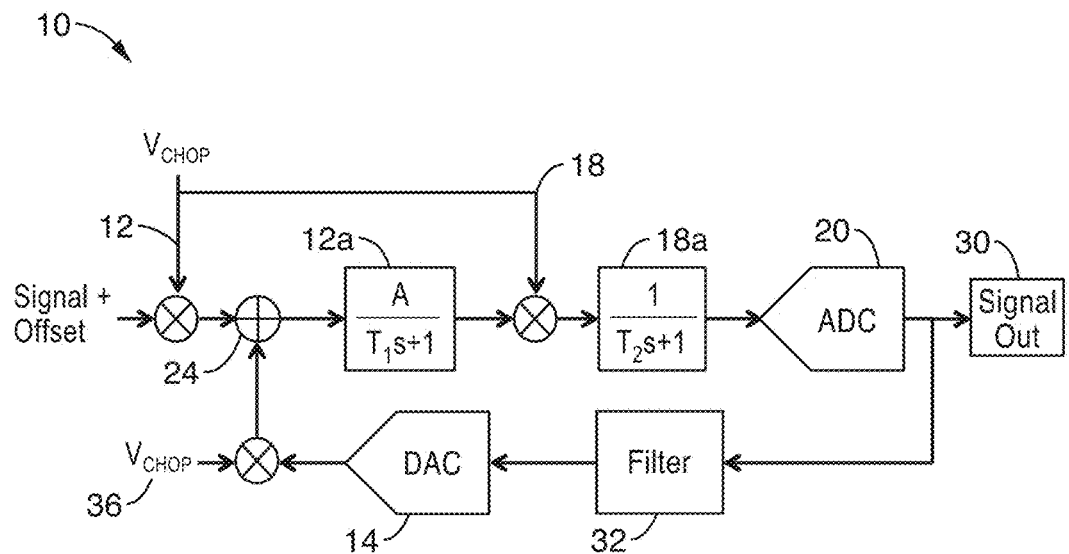
FIG. 7 is a schematic diagram of the behavioral model of ECoG front-end of FIG. 1.

FIG. 7 shows the block diagram for the behavioral model of the front-end 10 in closed loop, which was modeled using MATLAB and Simulink. The first low-pass filter 12*a* in the cascade represents the finite bandwidth of the chopper amplifier. The amplifier is preferably configured to be broadband with respect to the DAC 14 clock frequency of 1 MHz so that delta-sigma noise is allowed to pass through the chopper amplifier. Filtering the delta-sigma signal prior to down-conversion will result in noise folding in-band, and therefore should be avoided.

Figure 8:
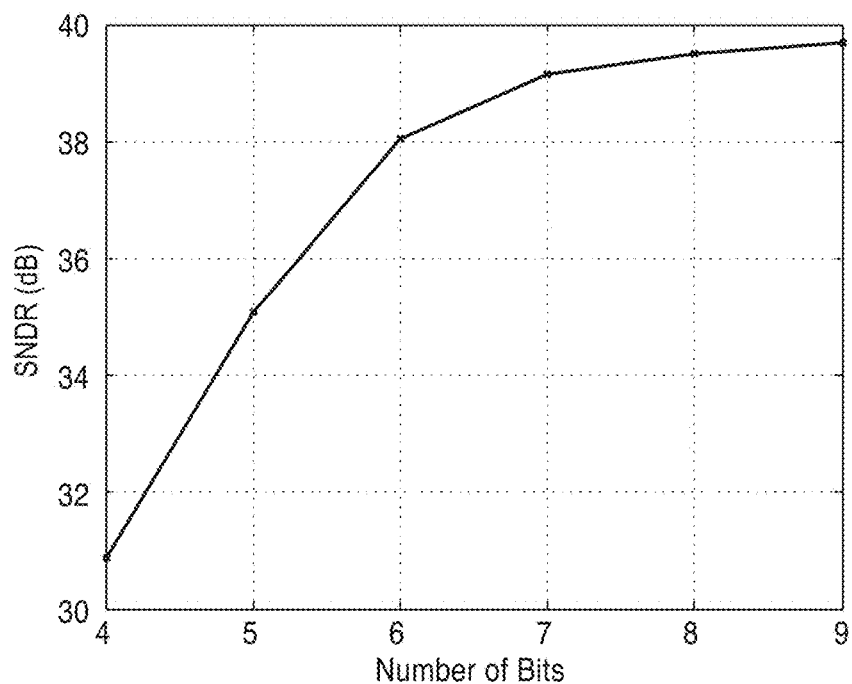
FIG. 8 is a plot of the SNDR vs. number of DAC bits in closed-loop.

An explicit low-pass filter 32 implemented after the down-modulation is illustrated in the plot of FIG. 8, which shows that once the system loop is closed, the large quantization noise at high frequency will fold back in-band. Although the quantization noise of the DAC 14 is below the in-band thermal noise floor, putting the system in feedback causes a degradation of the in-band SNDR by folding high-frequency noise back into baseband and degrading the noise floor by more than 4 dB for a 5-bit DAC.

Figure 9:
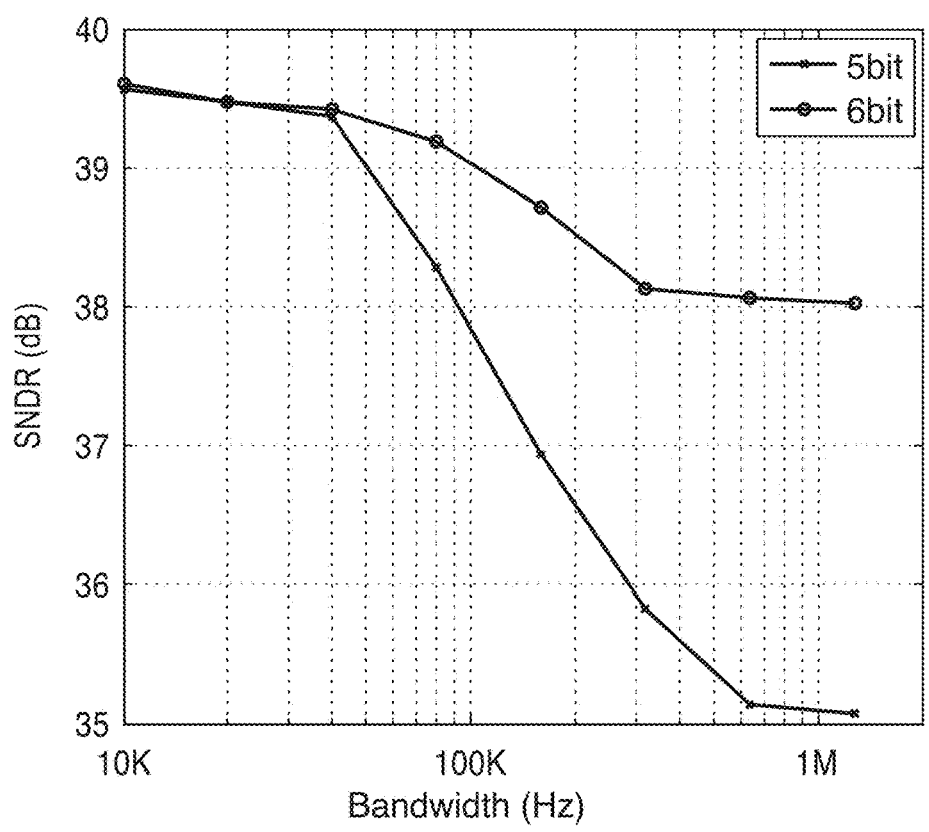
FIG. 9 is a plot of the SNDR vs. bandwidth for 5-bit and 6-bit DACs.

To overcome the noise folding a single-pole, filter 18*a* is placed in the forward path after the down-conversion chopper to filter the high-frequency quantization noise and improve the phase margin of the loop. In order to determine the desired bandwidth for this filter, the plot of FIG. 9 sweeps the bandwidth and shows that the thermal noise floor can be recovered for sufficiently low bandwidths. The noise floor degradation for a 6-bit DAC is less severe even in the absence of this filter since the quantization noise is 3 dB lower. To avoid the use of a low-pass filter a 6- or 7-bit DAC can be utilized at the expense of increased die area and lowered input impedance assuming the unit capacitor size is held constant.

The ECoG front-end 10 is configured to operate off of a 0.5 V supply voltage. Although designing low power, high dynamic-range circuits at low supply voltages is generally very challenging, these difficulties are mitigated in this context by two facts. First, since neural signals have a fixed low-amplitude input swing, amplifier swings can be reduced together with the supply. Because current consumption is determined by an absolute thermal noise specification, analog power consumption is reduced with decreased VDD. Second, the architecture described herein employs global mixed-signal feedback to reduce the dynamic range of each individual gain stage, and enables the use of open-loop circuit techniques that scale more gracefully to a low-supply environment.

Figure 10:
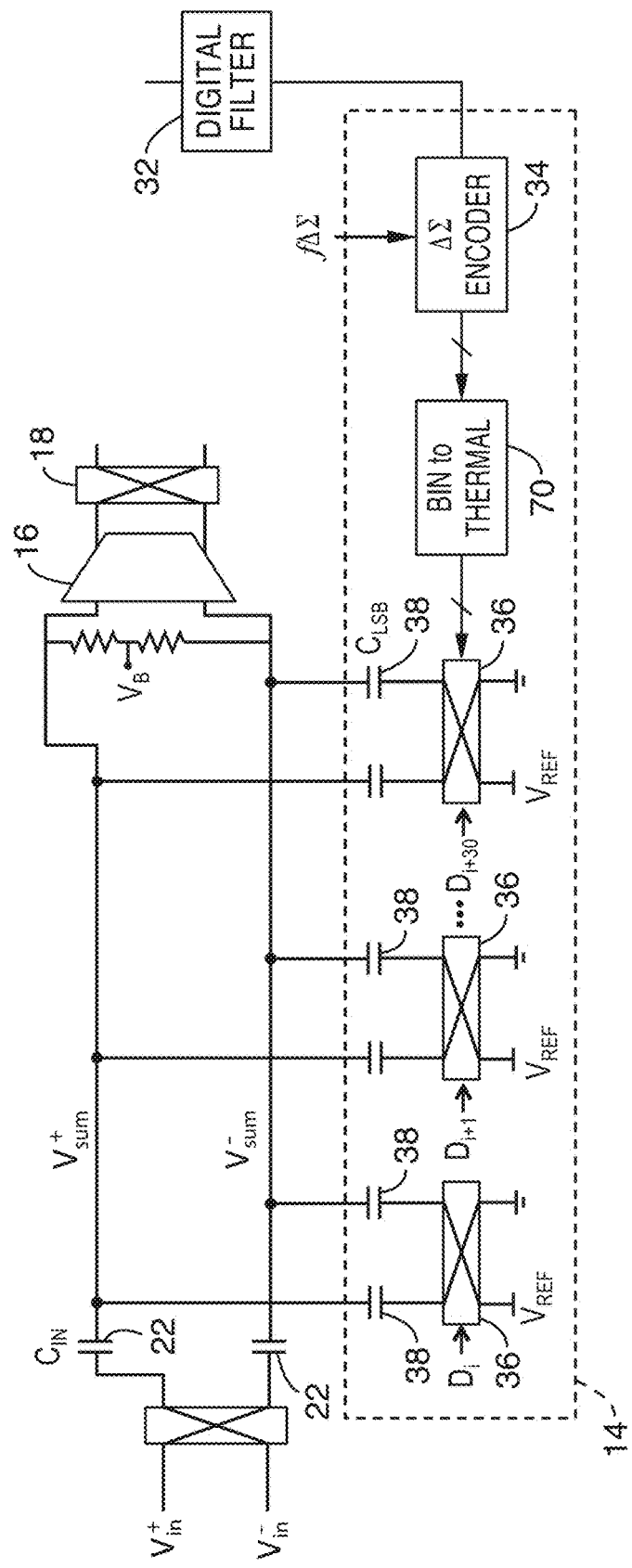
FIG. 10 is a schematic diagram of a simplified feedback DAC.

In order to cancel the up-modulated input offset, a 5-bit charge-distribution feedback DAC 14 is preferably employed. FIG. 10 shows an exemplary embodiment of a simplified schematic of the DAC 14. To minimize differential nonlinearity (DNL), the DAC 14 is thermometer coded via binary to thermal encoder 70 at the output of the Delta-Sigma encoder 34. To minimize area, each unit capacitor is minimum sized. The capacitors 38 are preferably implemented as metal-insulator-metal (MIM) capacitors that have relatively large minimum dimensions and 5% relative matching, thus maintaining low DNL. In this implementation, VREF=0.5 V and is tied to VDD. To cancel a full-scale voltage of 100 mV, or 50 mV on each differential input, CIN=10CDAC, where CDAC=31CLSB, and CLSB=41fF. The summation nodes are biased (VB) through a high resistance. The value of this resistance must be high enough such that the high-pass filter pole that it produces together with CIN is well below the lowest chopper frequency and thus out of the signal bandwidth.

Figure 11:
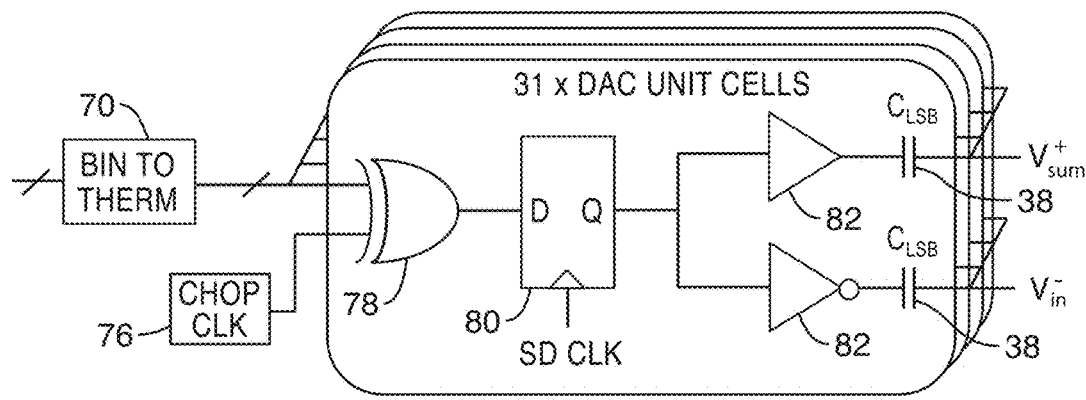
FIG. 11 is a schematic diagram of a DAC unit cell in accordance with the present disclosure.

Each unit cell of the feedback DAC 14 is comprised of two capacitors 38, $C_{LSB}$, that are switched in opposite polarity at each phase of the chop clock 76 (see FIG. 11). Since the chop clock 76 guarantees switching at every cycle, the capacitors 38 do not have to be explicitly reset. Thermometer-coded digital control bits, D, control the polarity of each unit cell modulating the amount of charge that is absorbed by the DAC 14 every time the chop clock changes. For example, if there is no offset present at the input, half of the capacitors on $V^+_{sum}$ would switch low-to-high, and the other half would switch high-to-low. These capacitors would neutralize and thus not cancel any offset from the input. In reality, since there are 31 unit capacitors, one capacitor should dither between the two states in order to realize zero offset cancellation.

FIG. 11 shows a simplified schematic of each unit cell of the DAC, which includes a SD clock 80, chopping amplifiers 82, and capacitors 38 at each unit cell. The Delta-Sigma encoder 34 (FIG. 10) provides a 5-bit output that is thermometer encoded 70 and distributed to the unit cells. An XOR gate 78 inverts the polarity at each phase of the chop clock 76. Since the logic is combinational, and driven by two inputs, one that is clocked at the Delta-Sigma clock frequency and the other at the chopper clock frequency, the DAC 14 is retimed to the highest clock frequency in order to avoid glitches. To ensure alignment of the DAC chopper 36 to the amplifier chopper 18, similar retiming is performed for the other chopper signals in the system. The signal is then buffered and inverted to provide an anti-phase signal to the negative input with the two paths designed for matched delay.

The final DAC capacitor driver is referenced to $V_{DD}$, but a lower voltage can be used at the cost of a reduced full-scale voltage of the DAC. Alternatively a lower ratio of $C_{IN}:C_{DAC}$ may be employed, however, this will cause $C_{DAC}$ to further attenuate the signal at the input of the amplification stage which will degrade noise performance. As designed, the attenuation of the DAC will degrade SNR by less than 0.5 dB.

To maximize capacitance density and minimize layout area, metal-insulator-metal (MIM) capacitors were used for both $C_{IN}$ and $C_{DAC}$. Since MIM capacitors are processed in the upper metal layers of the process, active circuits can be laid out in the lower layers. DAC unit cells are laid out below the $C_{DAC}$ capacitors and all other front-end circuits are laid out below the $C_{IN}$ capacitors. An additional metal layer below the MIM capacitors is used as a ground shield to minimize coupling of the digital circuits to the sensitive analog input.

The most common and simple 1/f noise reduction technique is to employ chopper stabilization. This technique up-modulates the signal by multiplying it with a square wave with an amplitude pattern of +1, −1, allowing the signal to be amplified at a higher frequency mitigating low-frequency interferers such as 1/f noise and amplifier offset. The signal must then be down-modulated and filtered in order to recover the original signal.

The consequences of the above are illuminated by analyzing the tradeoff between noise and amplifier input impedance when chopper stabilization is employed. An approximation is given by:

$$S_N \approx S_{n0}\left(1 + \frac{17 f_k}{2\pi^2 f_{chop}}\right) \qquad \text{Eq. 1}$$

where $S_{n0}$ is the thermal noise power spectral density, $f_k$ is the 1/f noise corner frequency and $f_{chop}$ is the chopper stabilization clock frequency. From this approximation alone, maximizing $f_{chop}$ seems optimal to minimize noise. In reality, a high $f_{chop}$ will lead to low input impedance, therefore an optimal value, which balances these two constraints, must be found. A good tradeoff can be found by selecting chopper frequency where $f_{chop}$ is at least 2 $f_k$, making the second term of Eq. 1 contribute only 20% or less to the total voltage noise.

Employing chopper stabilization creates a switched-capacitor resistance that degrades the input impedance of the amplifier. A significant advantage to using an open-loop architecture is that the effective input capacitance is reduced.

Figure 12A:
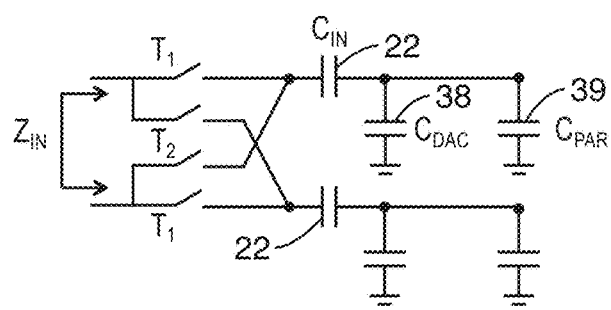
FIGS. 12A and 12B show simplified circuit diagrams of the switched-capacitor resistance of the input in-band chopper (FIG. 12A) and at DC chopper (FIG. 12B).
Figure 12B:
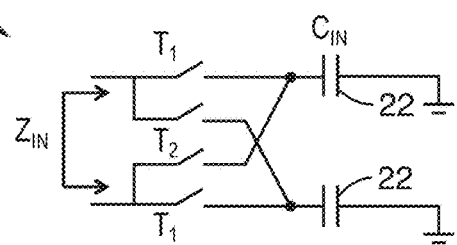

FIG. 12A and FIG. 12B show simplified circuit diagrams of the switched-capacitor resistance of the input in-band chopper (FIG. 12A) and at DC chopper (FIG. 12B).

In the circuit diagram of FIG. 12A, the input capacitance of the amplifier at each positive and negative input to ground is $C_{IN}$ 22 in series with $C_{DAC}$ 38+$C_{PAR}$ 39, where $C_{PAR}$ 39 is the parasitic capacitance on the summation node and is caused by bottom-plate capacitance, gate capacitance of the input devices and other layout parasitics. Since $C_{IN} \gg C_{DAC}$, the differential input resistance of the amplifier can be shown to be approximately $$|Z_{in}| \approx \frac{1}{4 f_{chop}(C_{DAC} + C_{PAR})}. \qquad \text{Eq. 2}$$

Since a high $f_{chop}$ will degrade the input impedance it is important to consider both capacitance and chopper frequency simultaneously. $Z_{IN}$ can be maximized in the following ways:

(1) Minimize $C_{DAC}$. In this implementation the size of $C_{DAC}$ is limited by the minimum sizing of a MIM capacitor, however, $C_{DAC}$ cannot be arbitrarily small and should be significantly larger than $C_{PAR}$ in order to not have its effect diminished. Therefore $C_{DAC}$ is a function of $C_{PAR}$.

(2) Reduce $f_{chop}$. This can be achieved by selecting a type of amplifier input transistor with low 1/f noise spectral density and by increasing the size of that device.

(3) Minimize $C_{PAR}$. This can be achieved by selecting a type of amplifier input transistor with low gate capacitance and by decreasing the size of that device.

Techniques (2) and (3) above are seemingly at odds with each other; therefore in selection and sizing of the amplifier input device, the quotient of the 1/f noise spectral density and capacitance $S_{1/f} \cdot C_{PAR}$ must be minimized. Standard threshold PMOS input devices were chosen in order to minimize this metric.

The input resistance of the front-end is chopper frequency ($f_{chop}$) dependent. At low frequency, the mixed-signal feedback loop becomes active, changing the impedance characteristics.

FIG. 12B shows an equivalent circuit model 12b for the input of the front-end at DC. The feedback loop tracks the DC voltage and cancels it at the summing nodes, creating a virtual ground. In this case, $C_{IN}$ dominates the input impedance characteristics of the front-end and the input impedance becomes:

$$|Z_{in}| \approx \frac{1}{2 f_{chop} C_{IN}}. \qquad \text{Eq. 3}$$

Since $C_{IN}$=10 $C_{DAC}$, the DC input resistance will be significantly lower than the impedance in-band. This lower impedance helps to attenuate the DC offset present at the electrodes and stabilize the baseline.

Figure 13:
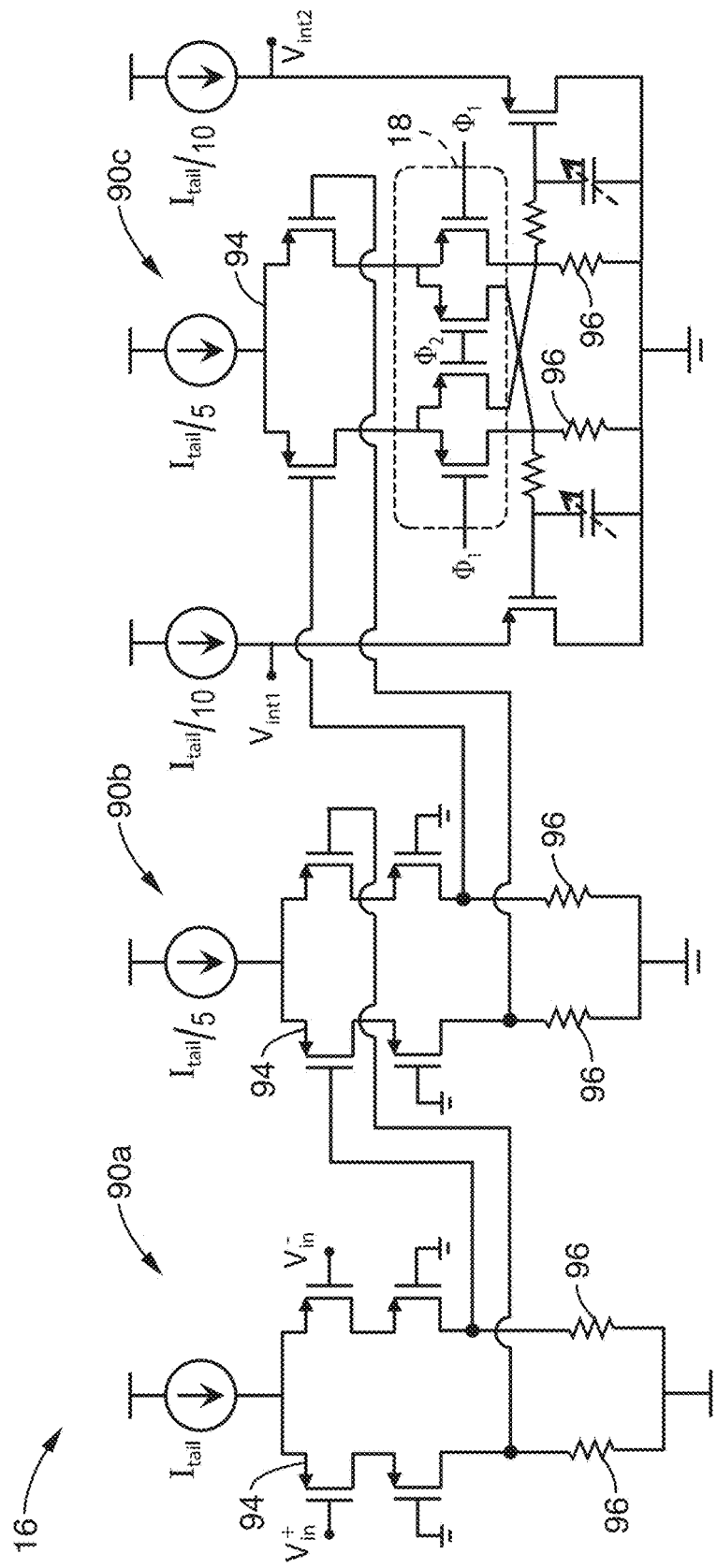
FIG. 13 is a schematic diagram of an amplifier and low-pass filter in accordance with the present disclosure.

Referring now to the amplifier 16 shown in the schematic diagram of FIG. 13, the forward path amplification is ideally broadband compared to the signal, at least 1-2 octaves above the Delta-Sigma modulation frequency. In order to achieve more than 3 MHz of bandwidth in approximately 2 μW of power dissipation, three cascaded low-gain stages 90a, 90b, and 90c were used. Each stage is comprised of a PMOS input differential pair 94, a PMOS cascode device to extend the bandwidth by decreasing the miller capacitance at each input gate-drain junction, and a resistive load comprised of polysilicon resistors 96. The polysilicon resistors 96 provide good noise performance and linearity at the cost of die area. Since the amplifier 16 must absorb the large swings of the chopper ripple and Delta-Sigma quantization noise, linearity became a higher priority than die area in this design.

A tunable single pole filter is realized at the output of the third gain 90*c* stage with the addition of tunable capacitance in parallel with the resistive load 96. The capacitors are realized with NMOS devices in depletion so that they remain linear throughout the signal range. Series resistance is added between the load resistor 96 and the capacitor to reduce the low-pass filter pole without affecting the gain and output swing of the stage 90*c*. The filter is tunable from a broadband 3.3 MHz down to 40 kHz. The chopper down-modulation switches 18 are shown in the dashed boxes of FIG. 13.

These devices act simultaneously as cascode devices and current-domain modulation devices. Down-modulating in the current domain is advantageous since chopping at a low impedance node in the current domain will not significantly degrade the gain of the stage; it can however increase the noise floor since the chopper switches are biased in saturation and therefore contribute 1/f noise. This scheme enables the seamless integration of a single-pole filter for filtering the Delta-Sigma DAC quantization noise. If the chopper switches were realized in the voltage domain at the output of the third stage, an additional buffer would be required to prevent the switched-capacitor resistance from affecting the filter pole frequency.

Finally, PMOS emitter-followers may be added to level-shift the output. The ADC 20 uses an NMOS-input differential pair driver, making DC level shifting from the chopper amplifier to the ADC driver necessary. The level shifters are sized to suppress their thermal and 1/f noise below the noise floor. Since they are single-ended, their current source devices also contribute significantly to their noise and must be sized accordingly. 1/f noise of the level-shifting stage accounts for 7% of the total input-referred noise when the chopper is clocked at 16 kHz. Redesigning the ADC and driver with PMOS inputs and eliminating this level-shifting stage can achieve further noise and power reduction.

The system 10 employs a similar current-driven, ring oscillator based ADC 20 as the Action Potential system with a more stringent linearity requirement due to the chopper ripple and DS DAC quantization noise that should be integrated. As shown in the schematic diagrams of FIG. 14A and FIG. 14B, the ADC driver 60 includes a differential-pair V-I converter 64 cascaded with a current-mode programmable gain block 62. The V/I converter load 64 is comprised of nine pairs of unit PMOS devices that can be individually connected either as cross-coupled pairs or as diode-connected devices. When N devices are cross-coupled, the differential mode load impedance seen by the V/I converter equals $1/(9-N)/g_{mp}$ (N<5 to maintain stability). The outputs of this block are connected to the gates of three matched unit PMOS devices 52*a*/52*b*. Changing N can therefore program the differential mode current gain without changing the power dissipation, enabling ease of compensation for varying input amplitudes, which are associated with the distance between the neuron and electrode. Cascode devices are used so that the variable load rather than the drain-source conductance of the input device dominates the gain. Variable degeneration resistors are used to further trade-off gain for linearity.

Since the ADC driver stage is cascaded after the chopper amplifier, its 1/f noise can significantly contribute to the 1/f noise of the entire front-end, therefore all devices are designed large for the purpose of suppressing 1/f noise. 1/f noise of the ADC driver accounts for 2% of the total input-referred noise power when chopped at 16 kHz, amounting to approximately 8.5 nVrms/√Hz across a 500 Hz bandwidth.

In order to keep the quantization noise well below the thermal noise floor an ADC resolution of 12 bits is desired. The ADC 20 employs the pseudo-differential, VCO-based architecture shown in FIG. 2 and whose basic operation is illustrated in FIG. 3.

Since the ADC should also quantize the range of the chopper ripple and DS DAC quantization noise, a full resolution of 14 bits is implemented in each of the counters. A 13-bit linear range is provided by each of the ring oscillators at 1 kS/s. Each oscillator is designed such that the minimum and maximum oscillation frequencies $f_{min}$ and $f_{max}$ satisfy $|f_{max}-f_{min}|>2^{12} f_s$ with $f_s=1$ kHz, therefore each differential output results in a dynamic range greater than 12 bits. Each counter is expressed as 14 bits to ensure monotonicity such that the counters never over-range twice. The counters are not reset with each clock period and are allowed to wrap. Digital correction is implemented to unwrap the codes prior to subtraction.

The counter output represents the average oscillator frequency over a period, corresponding to integration in the time domain and a sinc transfer function in the frequency domain. Thus the converter provides the desired boxcar sampling response, preventing aliasing of the wideband noise from the instrumentation amplifier. The box-car sampling characteristic introduces a second key benefit in this system, as it suppresses the shaped quantization noise from the DS DAC employed in the feedback. Because of the harmonic relation between the DS clock and the ADC clock, and the integrating nature of the ADC, the transfer between quantization noise and ADC output $NTF_Q(z)$ expressed in the 1 MHz clock domain is given by the modulator NTF cascaded with that of a 1000-tap moving average (MA) filter. For a DS noise transfer function of $NTF(z)=1-z^{-1}$, and $$NTF_Q(z) = NTF(z)MA(z) = \frac{1-z^{-1000}}{1000}.$$

The integrating characteristic of the ADC averages the DAC output bit-stream while performing the conversion, acting as first stage of decimation. Compared to the DS noise requirement in existing systems, this DS modulator has a 10× higher OSR. Therefore, its noise should be suppressed below a noise floor more than $10^4$ times smaller. As a result, although the high-frequency quantization noise from the DS modulator is greatly attenuated by the averaging of the ADC 20, a low-pass filter is used for further quantization noise suppression.

As seen in FIG. 1, the digital feedback comprises of a first-order integrating IIR filter 32 followed by a Delta-Sigma (DS) encoder 34. The feedback may be implemented with any low-pass IIR or FIR filter that satisfies the specifications of the overall closed-loop system transfer function and that the loop is stable. The integrator is clocked at a Nyquist rate of 1 kHz, while the DS modulator is clocked at 1 MHz. The higher ADC resolution demands higher resolution and word lengths in the digital filter, growing the area occupation.

Since the forward path gain is significantly increased, a greater degree of signal attenuation is used in the feedback path in order to maintain stability. A barrel shifter implements this attenuation with 12-bit tunability in addition to the built-in attenuation of $2^{17}$. The attenuation in the feedback path not only serves to stabilize the loop but also to tune the location of the high-pass filter pole.

Experimental Results

Figure 15:
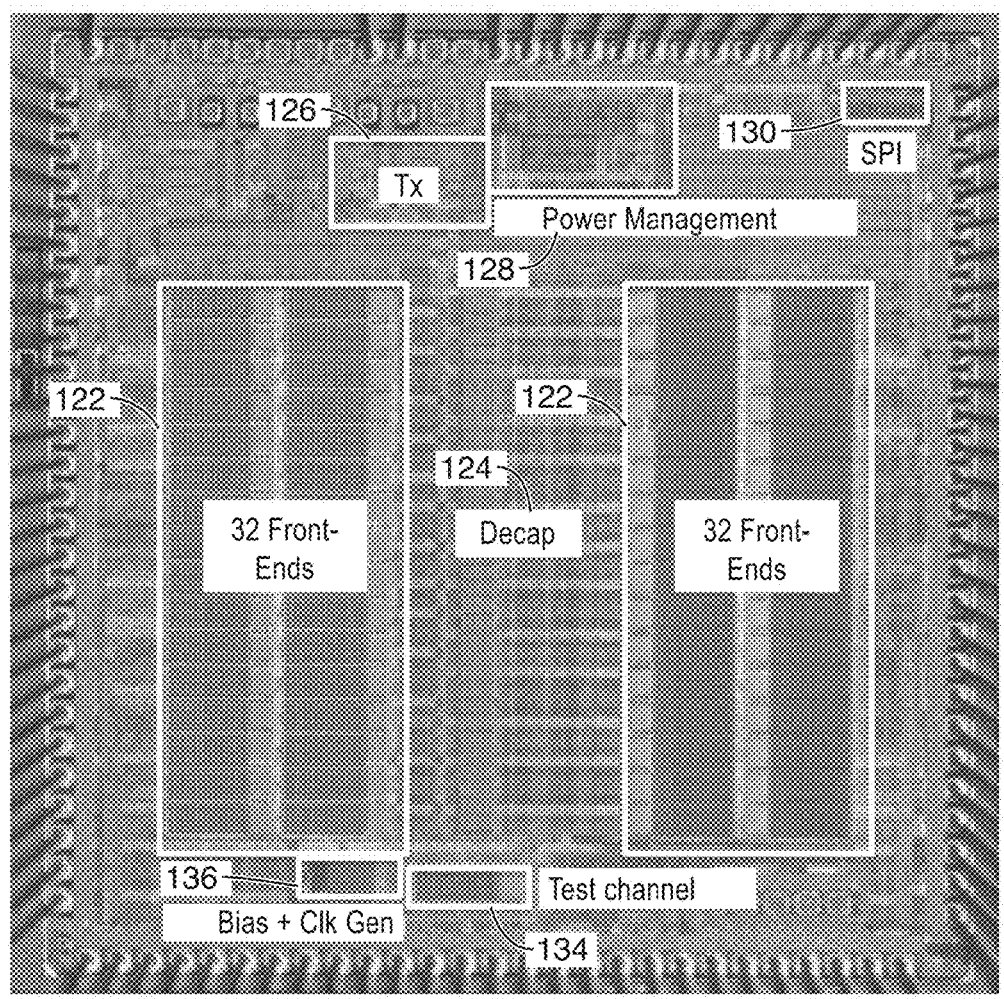
FIG. 15 is an image of a microphotograph of an exemplary 64-channel ECoG chip in accordance with the present disclosure.

A chip microphotograph 120 as shown in FIG. 15 was fabricated in a 65 nm 1P7M low-power CMOS process from ST Microelectronics. The chip contained 64 integrated front-ends 122 and one stand-alone front-end test block 134. Power conversion and management 128, wireless transmission 126, clock recovery and division as well as bias circuitry 136, decap 124 and SPI 130 are all integrated on the die. The total chip area is pad-limited to 2.4 mm×2.4 mm, the area of a single front-end is 0.025 mm² and the area of the 64 front-end array including routing is 1.6 mm². The total chip power consumption of the 64 front-ends plus the test-channel was measured to be 150 µW, and the power consumed by each front-end is 2.3 µW. The power dissipation is higher than designed since the polysilicon resistance was 20% smaller than their simulation value due to process variation, necessitating a higher current consumption in order to recover the lost gain.

Electrical characterization of the front-ends was performed by housing the die in a 124-pin 10 mm by 10 mm metal lead frame package connected to a PCB through a test socket. An Opal Kelly FPGA was used to buffer the serialized digital data stream from the front-end outputs. All measurements were performed through the full acquisition channel including the on-chip ADC. Post-processing of the digital outputs was performed using MATLAB. Differential sine wave inputs were produced using a Stanford Research Systems DS360 low-distortion signal generator and attenuated to proper input levels at the acquisition channel input. Power and input impedance was measured using a Kiethley 2612A source-meter.

Figure 16A:
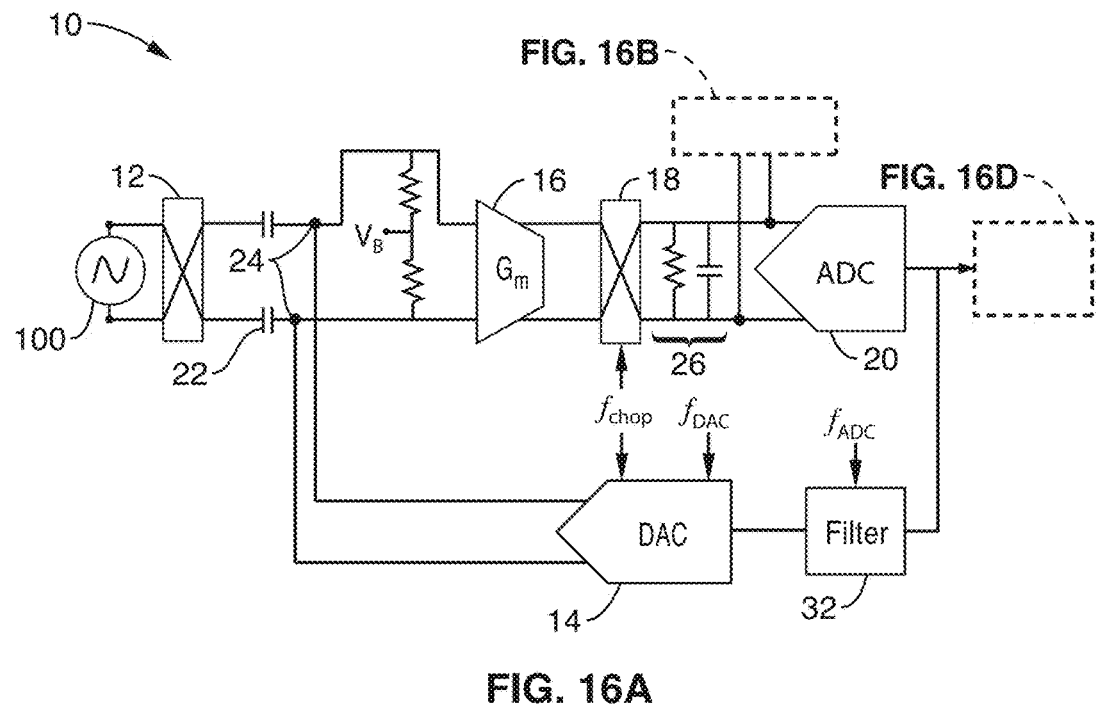
FIG. 16A shows a schematic diagram of an exemplary oscilloscope capture setup.
Figure 16B:
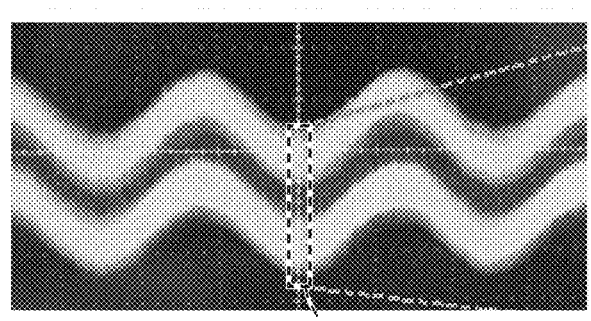
FIG. 16B, FIG. 16C and FIG. 16D show images of the oscilloscope capture setup of FIG. 1 of analog input to ADC and corresponding measured output of ADC from a 1 mVptp sine-wave stimulus.
Figure 16C:
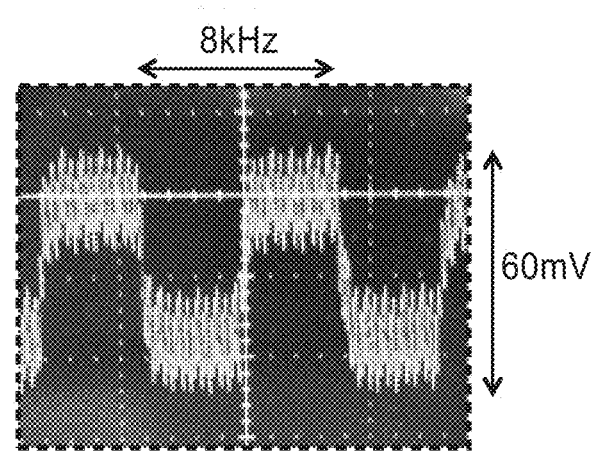
Figure 16D:
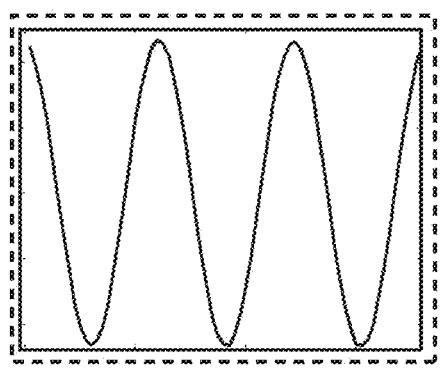

FIG. 16B, FIG. 16C and FIG. 16D show oscilloscope captures of the analog output waveform from a 1 mVptp stimulus as generated from the setup 10 of FIG. 16A (see also components of FIG. 1). Analog outputs are first buffered with unity-gain feedback amplifiers on chip, go through additional on-board amplification using AD8429 parts and are then observed on an Agilent DSO7104A oscilloscope 100. The front-end chopper frequency is set to 8 kHz and zero input offset is presented to the system.

The oscilloscope photos in FIG. 16B, FIG. 16C and FIG. 16D show that the analog output exhibits chopper ripple after down-modulation as a result of amplifier offset. Riding on top of the chopper ripple is the Delta-Sigma modulation noise, which is clearly visible after the low-pass filter. The bandwidth of the filter is set to its lowest frequency and measured to be 50 kHz. The total amplitude of the two superimposed signals is 60 mV after amplification. The 1 mVptp input signal is gained up and adds 30 mVptp making the total signal swing at the input to the ADC 90 mVptp. The corresponding ADC output waveform is also shown in the figure. It is clear from visual inspection that the ADC is able to filter both the chopper ripple and the Delta-Sigma noise to reproduce the original input sine wave. The remainder of this section will quantify the front-end performance.

Figure 17:
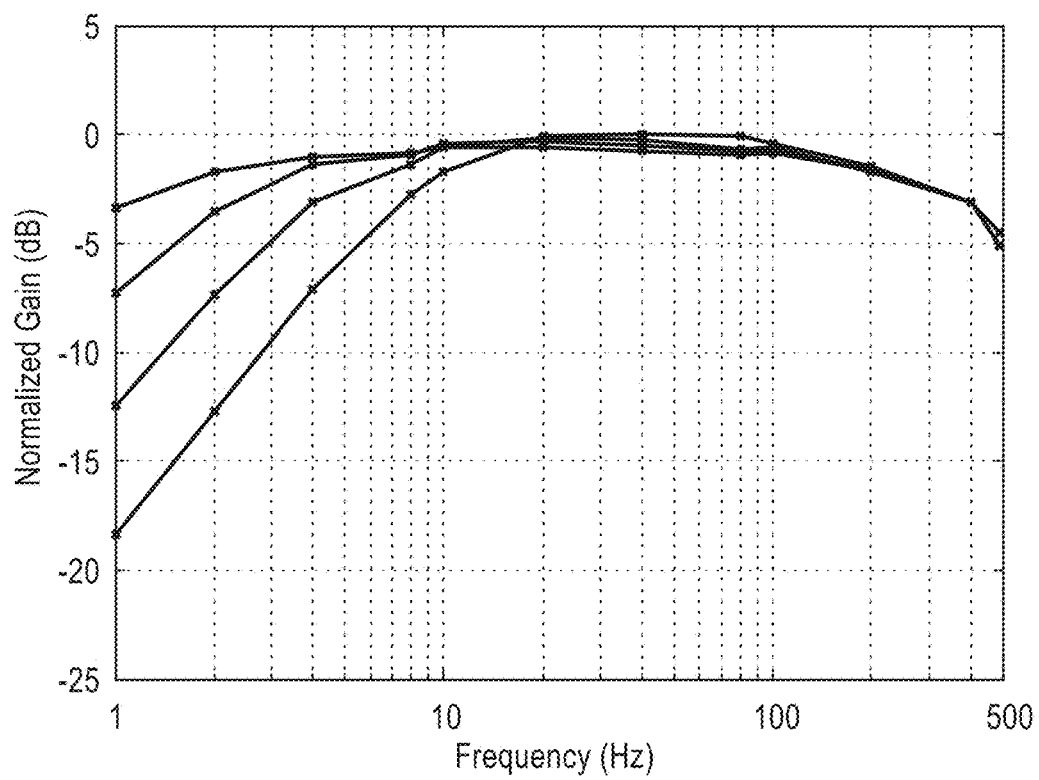
FIG. 17 is a plot of the measured front-end closed-loop transfer functions.

The measured closed-loop transfer functions of the ECoG front-end 10 from the input to the ADC output are shown in FIG. 17. The transfer function shows a first-order high-pass filter with a pole that is digitally programmable in the feedback loop. FIG. 17 shows transfer functions for four programmed states with poles at 8 Hz, 4 Hz, 2 Hz and 1 Hz. The low-frequency roll-off exhibits a −20 dB/decade slope. The high-frequency roll-off is due to the sinc transfer function of the A/D converter that is deterministic and can be compensated for in DSP if needed.

Figure 18:
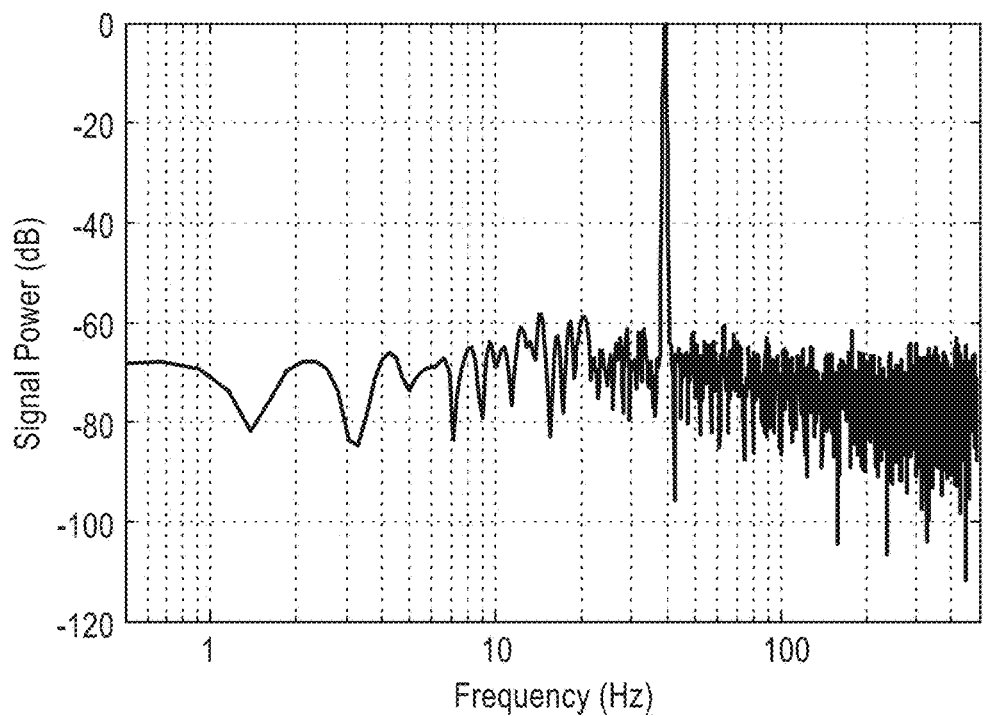
FIG. 18 is a plot of the power spectral density of output waveform with 0.5 mVptp sinusoidal input stimulus at 40 Hz.

FIG. 18 shows a plot of the measured output spectrum of the acquisition system for a 0.5 mVptp input sine wave at 40 Hz. The signal power is normalized to the peak power. At this input level no harmonic tones are visible above the noise floor.

Figure 19:
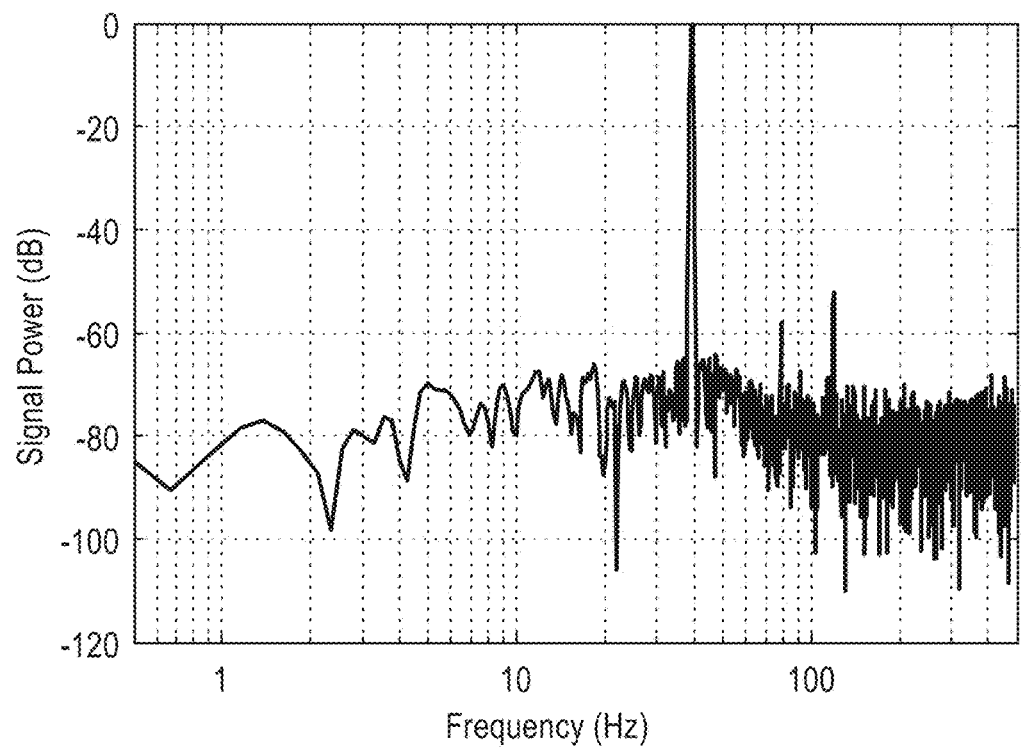
FIG. 19 is a plot of the power spectral density of output waveform with 1 mVptp sinusoidal input stimulus at 40 Hz.

FIG. 19 shows a plot of the normalized measured output spectrum of the acquisition system for a 1.0 mVptp input sine wave. At this input level second and third harmonic tones emerge in the spectrum. The complete system including the ADC exhibits a spurious free dynamic range (SFDR) of 52 dB and a total harmonic distortion (THD) of 0.4%.

Figure 20:
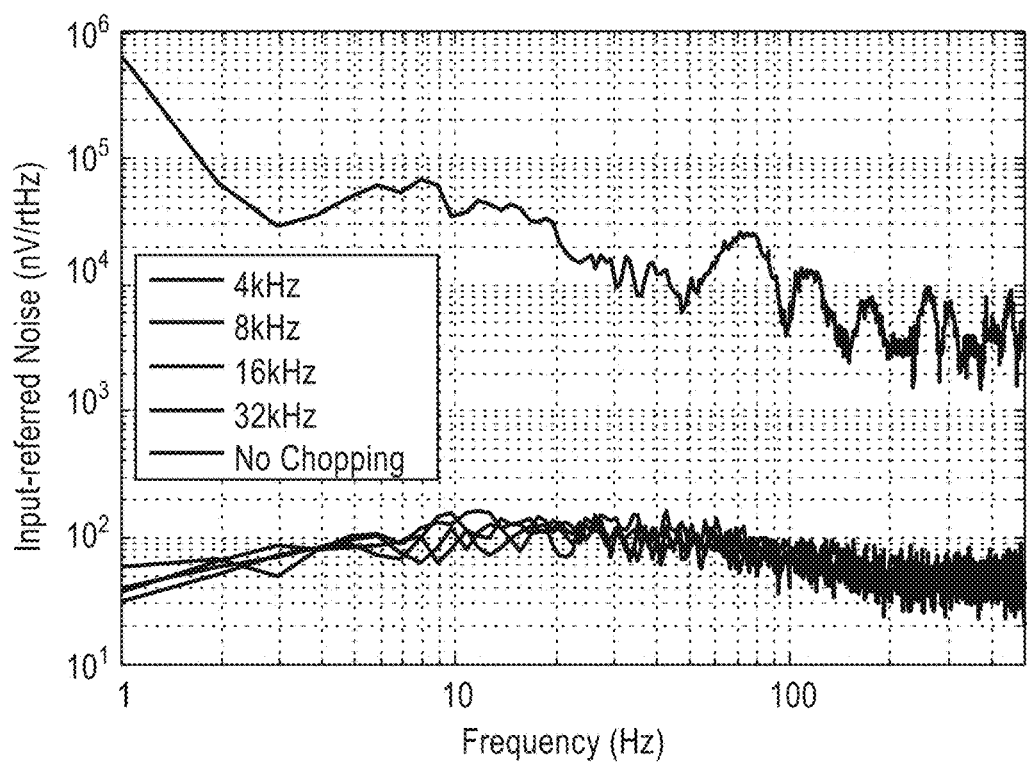
FIG. 20 is a plot of the input-referred noise power spectral density across a range of chopper modulation frequencies.

The input-referred noise spectral density is plotted in FIG. 20. Noise is plotted for a range of chopper frequencies as well as for the open-loop system with chopping disabled. In the absence of chopper stabilization, the noise spectral density of the amplifier is dominated by 1/f noise that is more than two orders of magnitude larger than the thermal noise floor. Integrated over the bandwidth, the noise of the amplifier without chopper stabilization would be 570 µV. This is substantially higher than the noise of the AP front-end integrated over the ECoG bandwidth since small devices are used at the input to avoid parasitic capacitance. In addition, the absence of chopper stabilization makes the system more susceptible to interferers such as 60 Hz noise, which impact the measured noise performance.

Figure 21:
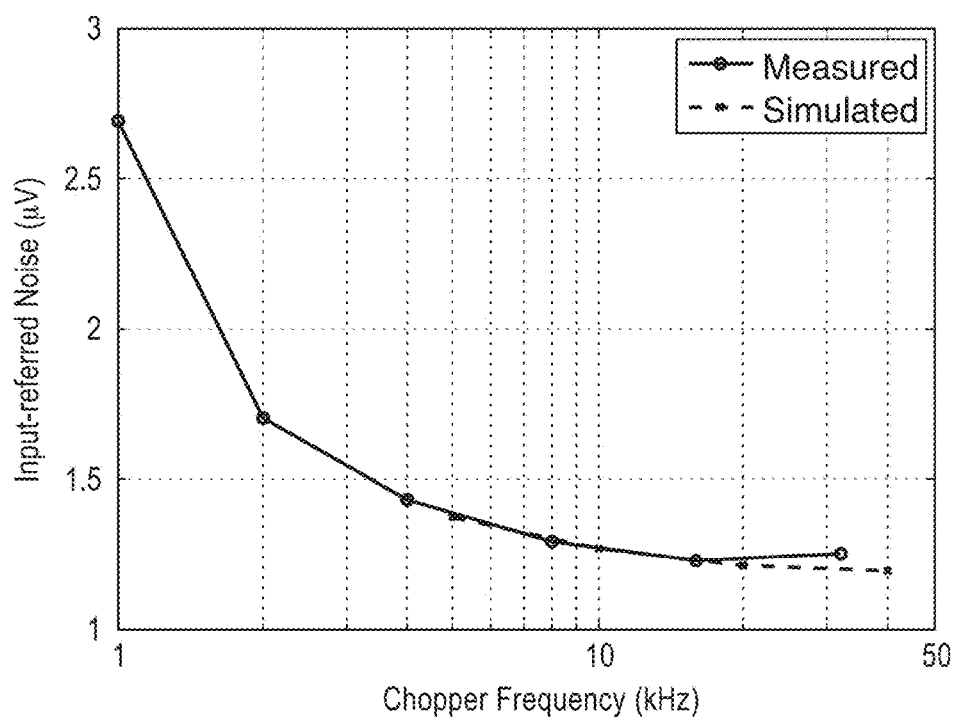
FIG. 21 is a plot of the integrated input-referred noise as a function of chopper frequency.

The chopper stabilized closed-loop system reduces the 1/f noise corner to 100-200 Hz. The input-referred noise integrated over the 500 Hz bandwidth is plotted in FIG. 21. Simulated values are plotted in the figure for comparison and show good agreement with the measured values. Higher chopping frequencies lower the 1/f noise corner frequency and reduce total input-referred noise. Chopping at frequencies beyond the inherent 1/f noise corner results in a diminished return in noise performance. Table 1 shows the exact measured values of input-referred noise for several operating frequencies of interest. Since the chopper stabilization frequency affects input impedance adversely, it is important to choose the lowest frequency that still meets the required noise performance. Since operating at 16 kHz only yields a 5% improvement in noise floor, 8 kHz is chosen as the operating point for this system. Should higher input impedance be required, operating at 4 kHz will double the input impedance with a 10% penalty in noise performance.

Operating at an 8 kHz chopping frequency, the Noise Efficiency Factor (NEF) of the entire front-end, including power dissipated in the ADC is 4.76 and the corresponding Power Efficiency Factor (PEF) is 11.3. The amplifier alone consumes 1.4 µW. Assuming the stand-alone amplifier would have the same noise performance as the full system (in reality the noise would be less), the NEF of the amplifier alone becomes 3.7 when chopped at 8 kHz becomes and the corresponding PEF is 6.9. If chopped at 4 kHz, the NEF of the complete system rises to 5.28 and the corresponding PEF becomes 13.9.

Figure 22:
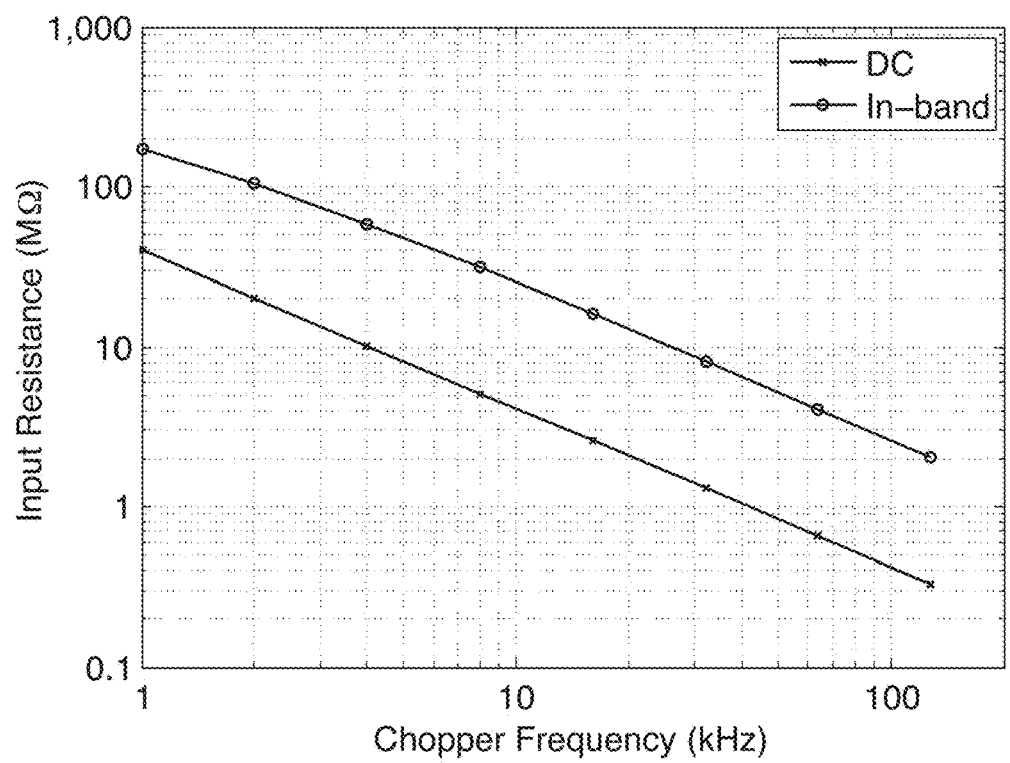
FIG. 22 is a plot of input resistance vs. chopper frequency for DC and in-band signals.
Figure 23:
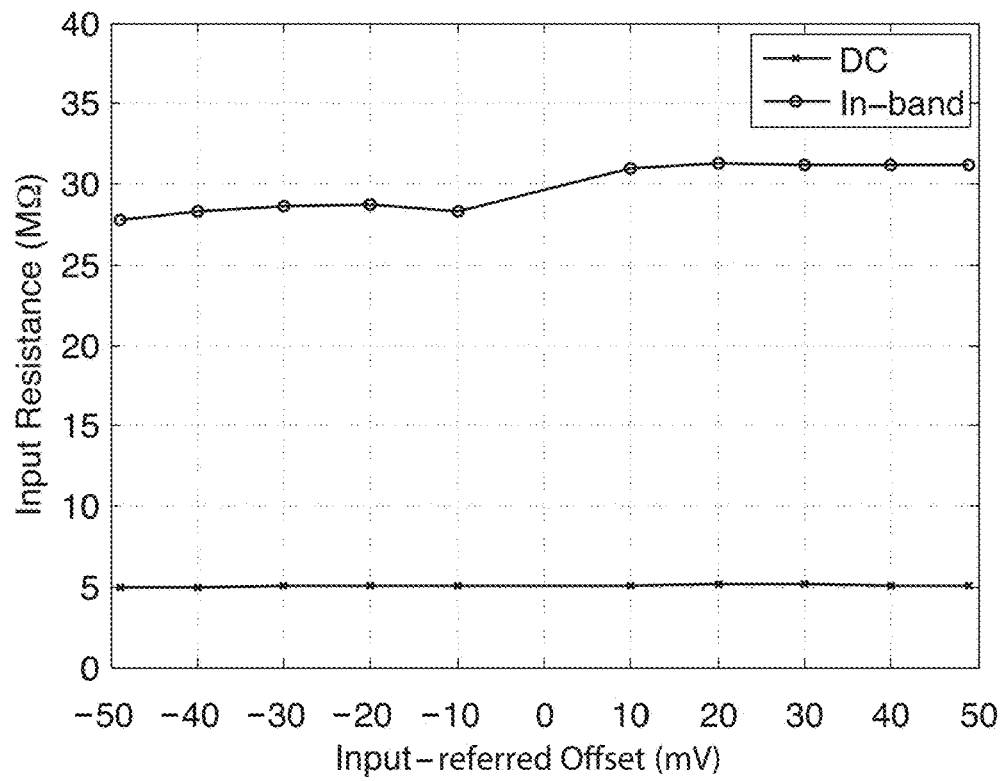
FIG. 23 is a plot of the input resistance vs. offset for DC and in-band signals at $f_{chop}$=8 kHz.

Input impedance was measured for all possible frequencies of chopper stabilization and plotted in FIG. 22. The measurements were made at DC and at 100 Hz (designated "in-band"). FIG. 23 plots input resistance vs. input-referred offset for a constant chopper frequency of 8 kHz. The calculated input resistances at DC and in-band are 4.9 MΩ and 25 MΩ respectively. The DC input resistance shows good agreement with calculation and stays constant to within 5% across all offset values. The in-band resistance shows agreement with calculation to within 10% and is constant to within 10% for the full range of input offsets. The capacitance that defines the in-band input impedance is significantly smaller than the capacitance that defines the DC impedance, and is therefore more susceptible to mismatch, although the discrepancy may also account for measurement error.

The full-scale range of the DAC was measured and found to be able to cancel a total of 98.6 mV. The lowest offset cancelled was −49.1 mV and the highest offset cancelled was +49.5 mV.

Finally, common-mode rejection ratio (CMRR) and power supply rejection ratio (PSRR) were measured for the complete system in feedback with a chopper stabilization frequency of 8 kHz. An in-band frequency of 60 Hz was chosen for the analysis since it corresponds to a well-known interferer and is well within the bandwidth of the system. CMRR was measured by connecting both inputs to an input sine wave generator, which produced a 50 mVptp sine wave at 60 Hz. The differential gain was measured through the ADC and determined by taking the spectrum of the output signal and compared to a differential input at 1 mVptp. The CMRR was measured to be 88 dB.

PSRR was measured in a similar fashion to CMRR with a 10 mVptp, 60 Hz sine wave with 0.5 V mean at the power supply pin. With the inputs grounded, the PSRR was measured to be 67 dB. The measured PSRR remained stable over a range of DC offsets applied at the input. It is possible to improve the PSRR of the system by decoupling the DAC reference from $V_{DD}$.

The ECoG front-end of the present disclosure was shown to have significant performance improvement as compared to state of the art designs from industrial and academic researchers. By employing a digitally-intensive system, and combining it with 1/f noise cancellation techniques, the area of the entire signal acquisition chain, including the ADC, is reduced to 0.025 mm². This is over an order of magnitude smaller than the smallest ECoG/EEG amplifiers reported to date. State-of-the art noise efficiency is achieved and together with a reduced power supply, this work achieves the best-reported PEF; three times lower than state-of-the-art designs. The small area enables the highest degree of integration achieved to date in low-frequency high-precision bio-signal acquisition with a 64-channel array in only 1.6 mm² of active silicon area with no external components required. The low supply voltage and a power-efficient design enable a highly scaled system with power levels easily achieved through wireless power coupling across a human skull.

Figure 24:
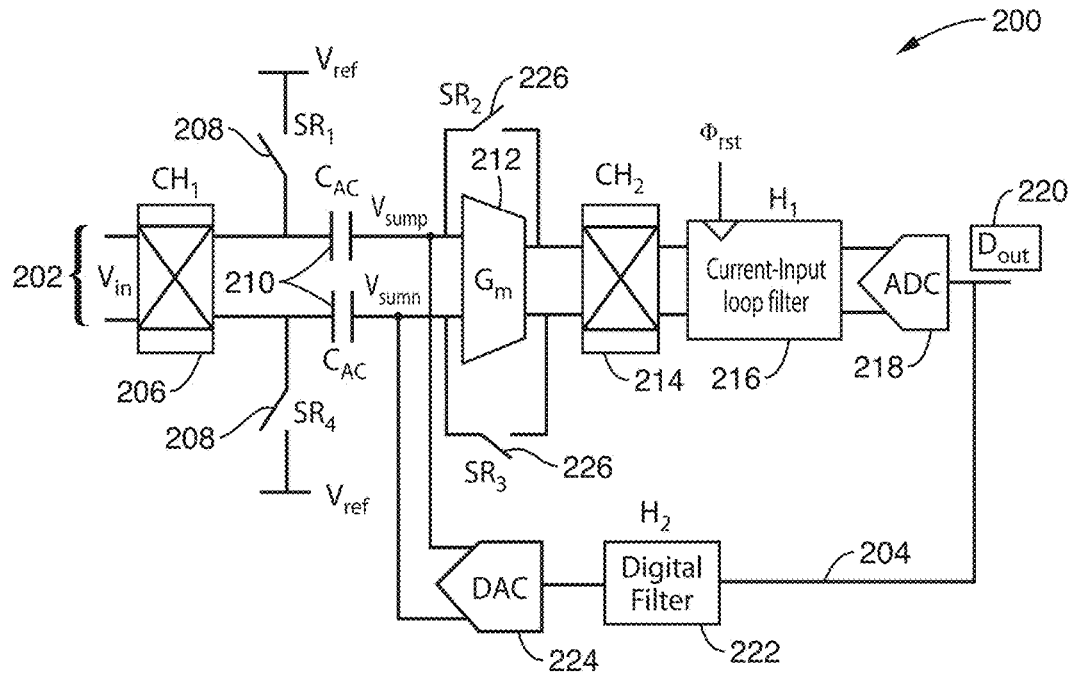
FIG. 24 shows a schematic view of a system incorporating a neural recording IC with a feedback loop.
Figure 25:
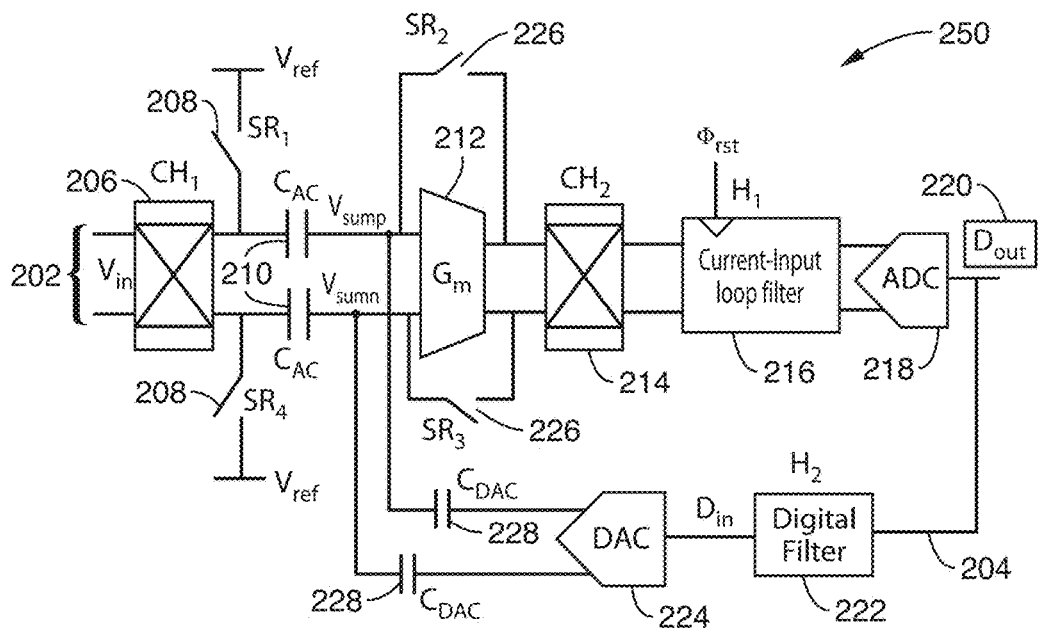
FIG. 25 shows a schematic view of a second embodiment of a neural recording IC incorporating a continuous time voltage-to-current converter, switched capacitor, and mixed-signal feedback path.
Figure 26:
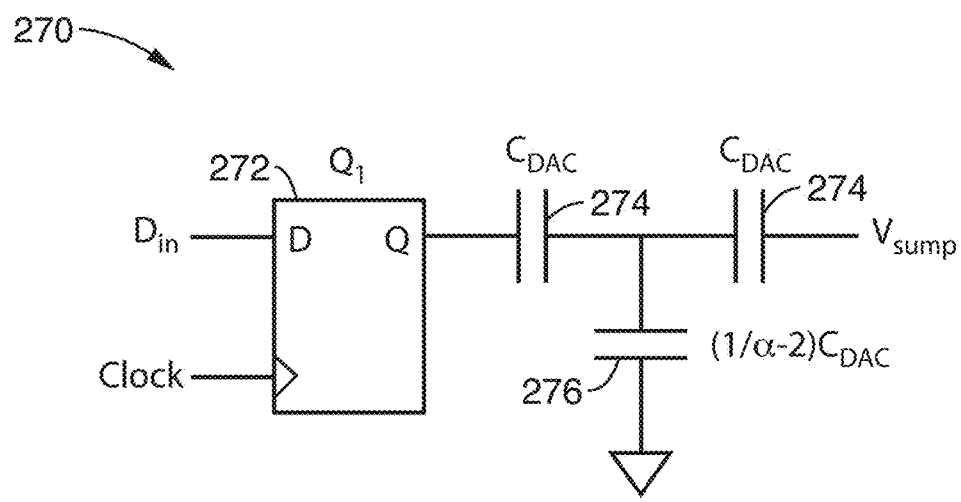
FIG. 26 shows a schematic diagram of a third embodiment using a capacitive T-network.

FIG. 24 through FIG. 26 illustrate additional alternative embodiments for a neural recording system with extended linear range, precise gain and increased input impedance in accordance with the present description.

FIG. 24 shows a schematic view of a system 200 incorporating a neural recording IC comprising a feedback loop. The forward path 202 of the feedback loop comprises a chopper-stabilized voltage-to-current converter, where the chopper down-modulation is applied to the output current, followed by a current-input loop filter 216 and an analog-to-digital converter 218.

The feedback path 204 comprises a digital filter 222 and a D/A converter (DAC) 224. In system 200, transconductor $G_m$ 212 performs a voltage-to-current conversion and drives the current input loop filter $H_1$. The current input loop filter 216 is preferably (but not exclusively) an integrator, and provides low-frequency gain. The transconductor 212 is chopper-stabilized by analog multipliers $CH_1$ 206 and $CH_2$ 214, and driven by frequency $f_{CHOP}$. Since the transconductor 212 is embedded in a feedback loop, system 200 directly digitizes the electrode signal plus offset, and can achieve very large linear range at low power consumption. The combination of the transconductor 212 and the current-driven loop filter 216 realize boxcar sampling of the input signal $V_{in}$, which suppresses noise at harmonics of the sample rate.

The output of the current-input filter 216 is digitized via ADC 218, and the digital output 220 is fed back into the forward path 202 after being processed by an optional digital filter $H_2$ 222, which can be used to further increase low-frequency loop gain. Switches $S_{R1}/S_{R4}$ 208 and $S_{R2}/S_{R3}$ 226 are closed during a reset phase $\phi_{rst}$ to store the offset of the transconductor 212 on input capacitors $C_{AC}$ 210, minimizing the chopper ripple due to transconductor offset. At the same time, all the capacitors in the loop filter are discharged by other switches. They are then left open for the remainder of each conversion so that sampled $KT/C_{AC}$ noise is converted into a much smaller chopper ripple. This enables using small values of $C_{AC}$. Since $Z_{in}=1/(4\ C_{AC}f_{CHOP})$, the use of small values of $C_{AC}$ enables higher input impedance than was previously possible.

FIG. 25 shows a second embodiment 250 of a neural recording IC, wherein a continuous-time voltage-to-current converter and a switched capacitor, mixed-signal feedback path are used in conjunction. In system 250, the feedback DAC 224 is implemented with a charge redistribution structure comprising DAC capacitors $C_{DAC}$ 228. As a result of the feedback and the use of the charge redistribution, the gain of the neural recorder 250 with the bandwidth of the feedback loop becomes $C_{AC}/(C_{DAC}V_{fsDAC})$, which is independent of the input signal, and can be made independent of temperature and manufacturing fluctuations. This enables precise gain matching and increased linear range compared to previously achievable values.

FIG. 26 shows a schematic diagram of a third embodiment of a neural recording IC 270, wherein capacitor $C_{DAC}$ 228 of FIG. 25 is replaced by a capacitive T-network comprising a pair of $C_{DAC}$ capacitors 274 and $(1/\alpha-2)\ C_{DAC}$ capacitors 276. The use of the capacitive T-network allows the realization of a smaller effective $C_{DAC}$ using large unit capacitors. As a result, the gain of the system can now be written as $C_{AC}/(<C_{DAC}\ V_{REF})$. Flip-flop $Q_1$ re-aligns the feedback signal to the system clock 272 to prevent glitches. Compared to the previous case shown in FIG. 25, for the same full-scale voltage and $C_{DAC}$ value, a smaller $C_{AC}$ value can be used, which results in even higher input impedance.

The circuit architectures and methods described herein are shown configured for electrocorticography signal acquisition and digitization of brain signals from electrocorticography (ECoG) electrode arrays. ECoG electrode arrays that interface with brain or other body tissues have signals and characteristics similar to those that can be acquired through electroencephalography (EEG) or through intracortical local-field potentials (LFP). Therefore the architectures and methods described herein can be used to record any low-frequency neural signals that require low-noise readout electronics. Furthermore, the methods and systems of the present disclosure may be used more generically to acquire small signals from capacitive sensor interfaces. Examples of such sensors include gyroscopes and accelerometers.

From the description herein it will be appreciated that the inventive circuit architecture can be embodied in the form of an application specific integrated circuit (ASIC) or other device using conventional CMOS fabrication techniques known to those of skill in the art.

It will also be appreciated that the invention comprises an efficient signal acquisition digitizer having several novel aspects which include, but are not limited to, the following:

1. Innovative mixed-signal and digital circuit techniques are used to efficiently implement the large time constants required for filtering in a fine-line process.

2. The mixed-signal architectural choices enabled an order of magnitude in area reduction over state of the art with a 3× improvement on power efficiency.

3. This architecture with a low supply voltage of 0.5 V also helps achieve very low power performance.

4. The digital feedback allows large time constants required for filtering to be implemented in the digital domain rather than the analog domain so that they can be implemented with a low area and low power.

5. The sigma-delta modulated feedback DAC allows a low-area offset cancellation.

6. The VCO-based ADC provides a critical filtering component to cancel chopper ripple and sigma-delta noise.

7. An open-loop chopper stabilized amplifier provides low-noise operation with low power requirements.

8. The front-end circuit is suitable for ECoG, EEG, Action Potential recording, and other applications and achieves an order of magnitude in area reduction over state of the art while maintaining or improving upon the low-noise, power-efficient performance.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that the present disclosure encompasses multiple embodiments which include, but are not limited to, the following:

1. An apparatus for acquisition of signals from a sensor interface, comprising: a chopper-stabilized, open-loop amplifier, said amplifier comprising: one or more input up-modulation chopper switches; a $G_m$ stage; and one or more down-modulation chopper switches; said amplifier having an input for receiving signals from said sensor interface and an output; and wherein said output is fed back to the input through a low-pass filter.

2. The apparatus of any preceding embodiment, wherein said low-pass filter comprises a digital IIR low-pass filter.

3. The apparatus of any preceding embodiment, further comprising an ADC connected to the output of the amplifier.

4. The apparatus of any preceding embodiment, wherein the ADC comprises a VCO-based ADC.

5. The apparatus of any preceding embodiment, wherein the VCO ADC uses a voltage to current converter to drive a ring oscillator whose output is fed into a counter for quantization.

6. The apparatus of any preceding embodiment, wherein a quantization sample is taken at every clock cycle and subtracted from the previous quantization level to produce a digital output.

7. The apparatus of any preceding embodiment, wherein digital filter output is delta-sigma modulated and fed back to the input through an oversampled capacitor DAC.

8. The apparatus of any preceding embodiment, wherein the DAC has an output that is upmodulated through one or more chopper switches so that cancellation occurs in the up-modulated signal domain.

9. The apparatus of any preceding embodiment, wherein summation of the DAC and an input signal occurs after the input capacitors and the feedback DAC capacitors, at the input of the Gm amplification stage.

10. The apparatus of any preceding embodiment, wherein said input comprises acquisition of low-frequency biological signals.

11. The apparatus of any preceding embodiment, further comprising: an array of electrodes configured to interface with the brain or other body tissues to acquire biological or neurological signals.

12. The apparatus of any preceding embodiment, wherein the amplifier further comprises an R-C filter load.

13. A circuit for acquisition of signals from a sensor interface, comprising: a forward path comprising: an input up-modulation chopper module; an amplifier having an input coupled to the up-modulation chopper module; a down-modulation chopper module coupled to an output of the amplifier; and an ADC having an input coupled to the down-modulation chopper module and a digital output; and a mixed-signal feedback loop from the digital output to the amplifier input; wherein the mixed-signal feedback loop comprises a digital filter.

14. The circuit of any preceding embodiment, wherein the ADC comprises a VCO-based ADC.

15. The circuit of any preceding embodiment, wherein the VCO ADC uses a voltage to current converter to drive a ring oscillator whose output is fed into a counter for quantization.

16. The circuit of any preceding embodiment, wherein digital filter output is delta-sigma modulated and fed back to the input through an oversampled capacitor DAC.

17. The circuit of any preceding embodiment, wherein the DAC has an output that is upmodulated through one or more chopper switches so that cancellation occurs in the up-modulated signal domain.

18. The circuit of any preceding embodiment, wherein summation of the DAC and an input signal occurs after the input capacitors and the feedback DAC capacitors, at the input of the Gm amplification stage.

19. A circuit for acquisition of signals from a sensor interface, comprising: a forward path comprising: a chopper-stabilized voltage-to-current converter; wherein chopper down-modulation is applied to an output current of the converter; a current-input loop filter; and an ADC; and a mixed-signal feedback path emanating from a digital output of the ADC; the mixed-signal feedback path comprising a DAC having an output feeding back into the forward path.

20. The circuit of any preceding embodiment, wherein the mixed-signal feedback path comprises a digital filter.

21. The circuit of any preceding embodiment, wherein the voltage-to-current converter comprises a transconductor that performs a voltage-to-current conversion and drives the current-input loop filter.

22. The circuit of any preceding embodiment, wherein the transconductor is chopper-stabilized by one or more analog multipliers.

23. The circuit of any preceding embodiment, wherein the forward path comprises a continuous-time voltage-to-current converter and the mixed-signal feedback path comprises a switched capacitor.

24. The circuit of any preceding embodiment, wherein the DAC and switched capacitor comprise a charge redistribution structure.

25. The circuit of any preceding embodiment, wherein the mixed-signal feedback path comprises a capacitive T-network.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Chopper Frequency | Input-referred Noise |
|---|---|
| 4 kHz | 1.43 µV |
| 8 kHz | 1.29 µV |
| 16 kHz | 1.23 µV |

What is claimed is:

1. A circuit for acquisition of sensor signals from a sensor interface, comprising:
 a forward path comprising:
  a chopper-stabilized voltage-to-current converter having an output current;
  a down modulation chopper configured to apply chopper down-modulation to the output current of the voltage-to-current converter;
  a current-input loop filter; and
  an analog to digital converter (ADC);
 a mixed-signal feedback path from a digital output of the ADC to an input of the forward path;
  the mixed-signal feedback path comprising a digital to analog converter (DAC) generating an analog signal; and
  an up-modulation chopper circuit configured to up-modulate the analog signal and having an output feeding back into the forward path, the circuit for acquisition of sensor signals configured to directly digitize the sensor signals plus offset;
 a first pair of switches coupled to the input of the forward path; and
 a second pair of switches coupled across an input of the chopper-stabilized voltage-to-current converter to an output of the chopper-stabilized voltage-to-current converter, the first pair of switches and second pair of switches configured to reset the circuit during a reset phase between signal samples.

2. A circuit as recited in claim 1, wherein the circuit further comprises a digital Infinite Impulse Response (IIR) low-pass filter.

3. A circuit as recited in claim 1, wherein the ADC comprises a Voltage Controlled Oscillator (VCO) ADC.

4. The circuit as recited in claim 3, wherein the VCO ADC comprises:
 a ring oscillator.

5. A circuit as recited in claim 1, wherein the DAC is an oversampled capacitor DAC.

6. A circuit as recited in claim 1, wherein the up-modulation chopper circuit comprises a plurality of chopper switches.

7. A circuit as recited in claim 1, wherein the sensor interface signals comprise low-frequency biological signals.

8. A circuit as recited in claim 7, further comprising:
   an array of electrodes connected to the sensor interface and configured to interface with body tissues to acquire at least one of a biological signal and a neurological signal.

9. A circuit as recited in claim 1, wherein the mixed-signal feedback path comprises a digital filter.

10. A circuit as recited in claim 1, wherein the voltage-to-current converter comprises a transconductor that performs a voltage-to-current conversion and drives the current-input loop filter.

11. A circuit as recited in claim 10, wherein the transconductor is chopper-stabilized by one or more analog multipliers.

12. A circuit as recited in claim 1, wherein the chopper-stabilized voltage-to-current converter comprises a continuous-time voltage-to-current converter and the mixed-signal feedback path comprises a switched capacitor.

13. A circuit as recited in claim 12, wherein the DAC and the switched capacitor comprise a charge redistribution structure.

14. A circuit as recited in claim 1, wherein the mixed-signal feedback path comprises a capacitive T-network.

* * * * *